US009801922B2

(12) United States Patent
Spitz et al.

(10) Patent No.: US 9,801,922 B2
(45) Date of Patent: Oct. 31, 2017

(54) COMPOSITIONS AND METHODS OF TREATING CANCER

(75) Inventors: Douglas R. Spitz, Iowa City, IA (US); Michael K. Schultz, Iowa City, IA (US); Kyle Kloepping, Iowa City, IA (US); Yueming Zhu, Iowa City, IA (US); Nukhet Aykin-Burns, Iowa City, IA (US); Max S. Wicha, Ann Arbor, MI (US)

(73) Assignees: UNIVERSITY OF IOWA RESEARCH FOUNDATION, Iowa City, IA (US); REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 689 days.

(21) Appl. No.: 14/236,879

(22) PCT Filed: Aug. 2, 2012

(86) PCT No.: PCT/US2012/049375
§ 371 (c)(1),
(2), (4) Date: Apr. 25, 2014

(87) PCT Pub. No.: WO2013/019975
PCT Pub. Date: Feb. 7, 2013

(65) Prior Publication Data
US 2014/0228290 A1    Aug. 14, 2014

Related U.S. Application Data

(60) Provisional application No. 61/514,640, filed on Aug. 3, 2011.

(51) Int. Cl.
| *A61K 38/17* | (2006.01) |
| *A61K 31/19* | (2006.01) |
| *A61K 31/341* | (2006.01) |
| *A61K 31/41* | (2006.01) |
| *A61K 31/662* | (2006.01) |
| *A61K 31/675* | (2006.01) |
| *A61K 31/7004* | (2006.01) |
| *A61K 45/06* | (2006.01) |

(52) U.S. Cl.
CPC .............. *A61K 38/17* (2013.01); *A61K 31/19* (2013.01); *A61K 31/341* (2013.01); *A61K 31/41* (2013.01); *A61K 31/662* (2013.01); *A61K 31/675* (2013.01); *A61K 31/7004* (2013.01); *A61K 45/06* (2013.01)

(58) Field of Classification Search
CPC .................................................. A61K 31/662
See application file for complete search history.

(56) References Cited

U.S. PATENT DOCUMENTS

2008/0032940 A1* 2/2008 Kalyanaraman ....... A61K 31/66
514/34
2011/0053938 A1 3/2011 Foley et al.

OTHER PUBLICATIONS

Dai et al., Malignant Cells Can Be Sensitized to Undergo Growth Inhibition and Apoptosis by Arsenic Trioxide Through Modulation of the Glutathione Redox System, 1999, Blood, vol. 93, No. 1, pp. 268-277.*
O'Dwyer et al., Phase I trial of buthionine sulfoximine in combination with melphalan in patients with cancer, 1996, J. Clin. Oncol., vol. 14, No. 1, pp. 249-256.*
Smith et al., Delivery of bioactive molecules to mitochondria in vivo, 2003, PNAS, vol. 100, No. 9, pp. 5407-5412.*
Ahmad, et al., "Mitochondrial O2*- and H2O2 mediate glucose deprivation-induced stress in human cancer cells", J Biol Chem 280, 4254-4263 (2005).
Aykin-Burns, et al., "Increased levels of superoxide and H2O2 mediate the differential susceptibility of cancer cells versus normal cells to glucose deprivation", Biochem J, 418(1), 29-37 (2009).
Birch-Machin, et al., "An evaluation of the measurement of the activities of complexes I-IV in the respiratory chain of human skeletal muscle mitochondria", Biochem Med Metab Biol 51(1), 35-42 (1994).
Bradford, et al., "A rapid and sensitive method for the quantitation of microgram quantities of protein utilizing the principle of protein-dye binding", Anal Biochem 72, 248-254 (1976).
Chen, "Mitochondrial membrane potential in living cells", Ann Rev Cell Biol 4, 155-181 (1988).
Fath, et al., "Enhancement of carboplatin-mediated lung cancer cell killing by simultaneous disruption of glutathione and thioredoxin metabolism", Clin Cancer Res 17 (19), 6206-6217 (2011).
Fath, et al., "Mitochondrial electron transport chain blockers enhance 2-deoxy-D-glucose induced oxidative stress and cell killing in human colon carcinoma cells", Cancer Biol Ther 8(13), 1228-1236 (2009).
Griffith, et al., "Determination of glutathione and glutathione disulfide using glutathione reductase and 2-vinylpyridine", Anal Biochem 106, 207-212 (1980).
Lowry, "Protein measurement with the Folin phenol reagent", J Biol Chem 193(1), 265-275 (1951).
Millard, et al., "Preclinical Evaluation of Novel Triphenylphosphonium Salts with Broad-Spectrum Activity", PLoS One vol. 5 (10), e13131, 1-18 (2010).
Patent Cooperation Treaty, International Searching Authority, Search Report and Written Opinion for PCT/US2012/49375, 15 pages Oct. 19, 2012.
Puck, et al., "Action of x-rays on mammalian cells. II. Survival curves of cells from normal human tissues", J Exp Med 106, 485-500 (1957).

(Continued)

*Primary Examiner* — Kortney L Klinkel
*Assistant Examiner* — Tori M Strong
(74) *Attorney, Agent, or Firm* — Viksnins Harris Padys Malen LLP

(57) ABSTRACT

The invention provides compositions and methods to treat cancer with an agent that increases reactive oxygen species (ROS) levels in cancer cell mitochondria ("an XTPP agent") or a pharmaceutically acceptable salt thereof, an inhibitor of hydroperoxide metabolism and a pharmaceutically acceptable diluent or carrier.

16 Claims, 14 Drawing Sheets

(56) References Cited

OTHER PUBLICATIONS

Simons, et al., "Inhibition of glutathione and thioredoxin metabolism enhances sensitivity to perifosine in head and neck cancer cells", J Oncol 2009, 519563, 10 pages (2009).

Smith, et al., "Animal and human studies with the targeted antioxidant MitoQ", Annals of the New York Academy of Sciences 1201, 96-103 (2010).

Spitz, et al., "Cytotoxicity and metabolism of 4-hydroxy-2-nonenal and 2-nonenal in H2O2-resistant cell lines. Do aldehydic by-products of lipid peroxidation contribute to oxidative stress?", Biochem J 267, 453-459 (1990).

* cited by examiner

| Treatment | ALDH + (% cells) of Alive Cell |
|---|---|
| Hoechst only | 0 |
| Control | 2.61±0.63 |
| BSO | 2.62±0.67 |
| AUR | 1.11±0.22 * |
| DTPP | 1.16±0.31 * |
| BSO+AUR | 0.45±0.43 * |
| BSO+DTPP | 0.65±0.24 * |
| BSO+AUR+DTPP | 0.17±0.09 * |

FIG. 16

| 24hour incubation NAC & DTPP | | | | | | | |
|---|---|---|---|---|---|---|---|
| NAC Standard (No DMSO) | Analytical Abs | NAC with DMSO 0.1% | Analytical Abs | NAC+DTPP | Analytical Abs | DTPP | Analytical Abs |
| 0mM | 0.1093 | | | | | | |
| 0.01mM | 0.1238 | | | | | | |
| 0.05mM | 0.1752 | | | | | | |
| 0.1mM | 0.2337 | 0.1mM | 0.22985 | 0.1mM | 0.22395 | 0.1mM | 0.10845 |
| 0.25mM | 0.436 | 0.25mM | 0.4128 | 0.25mM | 0.39535 | 0.25mM | 0.10905 |
| 0.5mM | 0.7722 | 0.5mM | 0.7103 | 0.5mM | 0.6854 | 0.5mM | 0.1094 |
| 1mM | 1.4528 | | | | | | |

| 1hour incubation NAC & AUR | | | | | | | |
|---|---|---|---|---|---|---|---|
| NAC Standard (No DMSO) | Analytical Abs | NAC with DMSO | Analytical Abs | NAC +AUR | Analytical Abs | AUR | Analytical Abs |
| 0mM | 0.1098 | | | | | | |
| 0.01mM | 0.1248 | | | | | | |
| 0.05mM | 0.1839 | 0.05mM | 0.148255 | 0.05mM | 0.2369 | 0.05mM | 0.16275 |
| 0.1mM | 0.2597 | 0.1mM | 0.2397 | 0.1mM | 0.3518 | 0.1mM | 0.20565 |
| 0.25mM | 0.4757 | 0.25mM | 0.42105 | 0.25mM | 0.7517 | 0.25mM | 0.3474 |
| 0.5mM | 0.8306 | 0.5mM | 0.7687 | 0.5mM | 1.3684 | 0.5mM | 0.5854 |
| 1mM | 1.5624 | | | | | | |

FIG. 17

| Treatment | nmol GSH/mg protein | nmol GSSG/mg protein | % GSSG |
|---|---|---|---|
| Control | 10.63 ± 4.03 | 0.06 ± 0.05 | 1.13 ± 1.01 |
| BSO | 1.79 ± 0.05 | 0.09 ± 0.01 | 4.88 ± 0.73 |
| AUR | 8.49 ± 1.34 | 0.15 ± 0.05 | 1.92 ± 1.09 |
| DTPP | 7.02 ± 0.83 | 0.26 ± 0.07 | 3.65 ± 0.94 |
| BSO+AUR | 1.25 ± 0.20 | 0.13 ± 0.02 | 10.81 ± 1.84 |
| BSO+DTPP | non-detectable | non-detectable | non-detectable |
| BSO+AUR+DTPP | non-detectable | non-detectable | non-detectable |

FIG. 18

COMPOSITIONS AND METHODS OF TREATING CANCER

RELATED APPLICATION

This application is a U.S. 371 application of PCT/US2012/049375, which was filed on Aug. 2, 2012, and claims the benefit of priority of U.S. Ser. No. 61/514,640 filed on Aug. 3, 2011, the entirety of which are incorporated herein by reference.

FEDERAL GRANT SUPPORT

The invention was made with government support under R01CA133114 and R01CA100045 awarded by the National Institutes of Health. The government has certain rights in the invention.

BACKGROUND

Most treatment plans for patients with cancer include surgery, radiation therapy, and/or chemotherapy. However, because of problems with such treatment plans, such as side-effects caused by radiation therapy and chemotherapy, additional methods are needed for treating cancer.

SUMMARY

The present invention provides a pharmaceutical composition comprising an XTPP agent that increases reactive oxygen species (ROS) levels in cancer cell mitochondria, an inhibitor of hydroperoxide metabolism, and a pharmaceutically acceptable diluent or carrier. Examples of reactive oxygen species include superoxide and hydrogen peroxide (i.e., $O_2^{-}$, $H_2O_2$).

In certain embodiments, the XTPP agent comprises a triphenylphosphonium (TPP) molecule or a pharmaceutically acceptable salt thereof. As used herein, the term triphenylphosphonium is any molecule containing a triphenylphosphine cation ($^+PPh_3$) moiety.

In certain embodiments, the XTPP agent is $^+PPh_3$-X—R Y$^-$;

wherein:

X is a $(C_2-C_{50})$alkyl;

R is H, $N_3$, triazole optionally substituted with one or more (e.g. 1 or 2) $(C_4-C_8)$alkyl or quinone optionally substituted one or more (e.g. 1, 2 or 3) $(C_1-C_6)$alkyl or —O$(C_1-C_6)$alkyl; and Y$^-$ is a counterion;

or a pharmaceutically acceptable salt thereof.

As used herein, the term alkyl is defined as a straight or branched hydrocarbon. For example, an alkyl group can have 2 to 50 carbon atoms (i.e., $(C_2-C_{50})$alkyl), 1 to 10 carbon atoms (i.e., $(C_1-C_{10})$alkyl), 1 to 8 carbon atoms (i.e., $(C_1-C_8)$alkyl) or 1 to 6 carbon atoms (i.e., $(C_1-C_6$ alkyl). Examples of suitable alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$) and decyl (—(CH$_2$)$_9$CH$_3$).

As used herein the term counterion is a pharmaceutically acceptable counterion such as a pharmaceutically acceptable anion (e.g. Cl$^-$, Br$^-$, I$^-$, CH$_3$SO$_3^-$, CF$_3$SO$_3^-$ or p-CH$_3$C$_6$H$_4$SO$_3$).

In certain embodiments, R imparts hydrophilicity or reactive properties cytotoxic to cancer cells.

In certain embodiments R is:

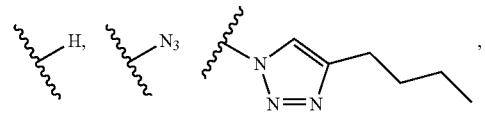

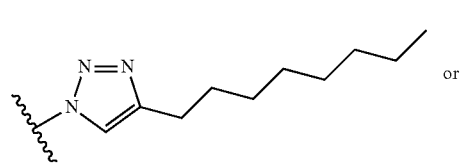

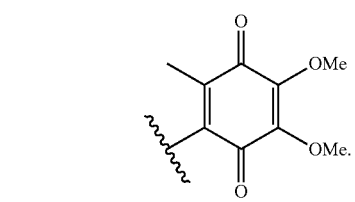

In certain embodiments, X is —(CH$_2$)$_{10}$—.

In certain embodiments, the XTPP agent that increases reactive oxygen species (ROS) levels in cancer cell mitochondria is:

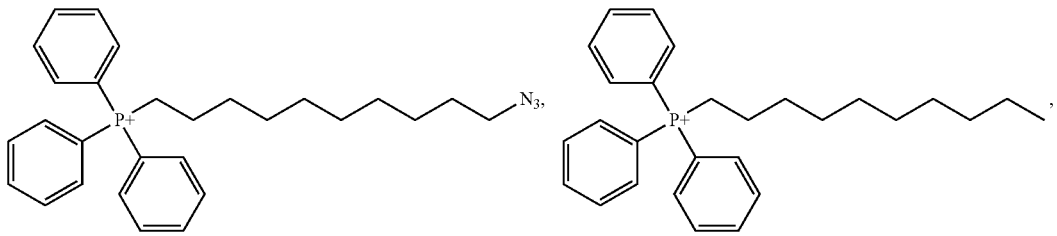

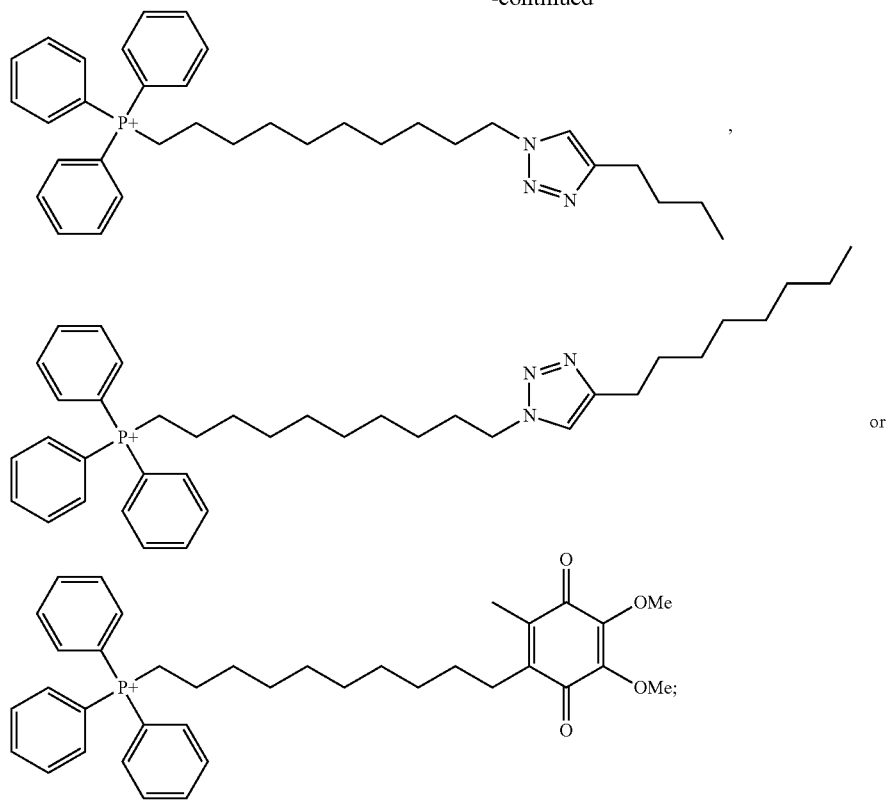

or a pharmaceutically acceptable salt thereof.

In certain embodiments, the pharmaceutical composition includes an inhibitor of glutathione synthesis or hydroperoxide metabolism comprising L-buthionine-[S,R]-sulfoximine (BSO), (S-triethylphosphinegold(I)-2,3,4,6-tetra-O-acetyl-1-thio-β-D-glucopyranoside Auranofin (AUR), or a combination of BSO and AUR. Other compounds that could also be used for this purpose include inhibitors of catalase (i.e. 3-aminotriazole), inhibitors of glucose metabolism (i.e., bromopyruvate and 2-deoxyglucose), inhibitors of peroxiredoxins, inhibitors of glutathione peroxidases, inhibitors of dehydrogenase enzymes that regenerate NADPH, inhibitors of thioredoxin reductase, inhibitors of glutathione reductase, inhibitors of glutathione transferases, and inhibitors of transcription factors as well as signal transduction proteins that regulate thiol mediated hydroperoxide metabolism (i.e., Nrf-2, AP-1, NFkB, AKT, ERK1/2, p38, EGFR, and IGFR). Another strategy to enhance the efficacy of a composition including DTPP with inhibitors of hydroperoxide metabolism would include feeding patients diets high in respiratory directed substrates including ketogenic diets, Atkins style diets, and pharmacological doses of IV vitamin C which would be expected to further enhance the differential metabolic production of pro-oxidants in cancer vs. normal tissues.

The present invention provides a method for treating cancer in a mammal, comprising administering a composition described above to the mammal. In certain embodiments, the agent that increases reactive oxygen species (ROS) levels in cancer cell mitochondria (also called "an XTPP agent" or "XTPP" herein) and inhibitor of hydroperoxide metabolism or glutathione synthesis are administered sequentially rather than in a single composition.

The present invention provides a method for inducing clonogenic cell killing and cellular apoptosis of a cancerous cell, comprising contacting the cancerous cell with an effective clonogenic cell killing or apoptosis-inducing amount of the composition described above. In certain embodiments, the XTPP agent and inhibitor of hydroperoxide metabolism or glutathione synthesis are administered sequentially rather than in a single composition.

The present invention provides a method for increasing the anticancer effects of a conventional cancer therapy (i.e., radio- and/or chemo-therapy) on cancerous cells in a mammal, comprising contacting the cancerous cell with an effective amount of the composition described above and administering an additional conventional cancer therapy modality. In certain embodiments, the additional cancer therapy is chemotherapy and/or radiation. In certain embodiments, the XTPP and inhibitor of hydroperoxide metabolism or glutathione synthesis are administered sequentially rather than in a single composition.

In certain embodiments of the methods described above, the composition does not significantly inhibit viability of comparable non-cancerous cells.

The present invention provides a method for selectively inducing oxidative stress in a cancer cell in a mammal in need of such treatment comprising administering to the mammal an effective amount of the composition described above. In certain embodiments, the XTPP and inhibitor of hydroperoxide metabolism are administered sequentially rather than in a single composition. In certain embodiments, the mammal is a human.

In certain embodiments of the methods described above, the cancer is breast cancer, prostate cancer, lung cancer, pancreas cancer, head and neck cancer, ovarian cancer, brain cancer, colon cancer, hepatic cancer, skin cancer, leukemia, melanoma, endometrial cancer, neuroendocrine tumors, carcinoids, neuroblastoma, tumors arising from the neural crest, lymphoma, myeloma, or other malignancies characterized by aberrant mitochondrial hydroperoxide metabolism. In certain embodiments, the cancer is the above cancers that are not curable or not responsive to other therapies. In certain embodiments the cancers are hormone dependent or hormone-independent epithelial cancers.

In certain embodiments of the methods described above, the tumor is reduced in volume by at least 10%. In certain embodiments, the tumor is reduced by any amount between 1-100%. In certain embodiments, the tumor uptake of molecular imaging agents, such as fluorine-18 deoxyglucose, fluorine-18 thymidine or other suitable molecular imaging agent, is reduced by any amount between 1-100%. In certain embodiments the imaging agent is fluorine-18 deoxyglucose, fluorine-18 thymidine or other suitable molecular imaging agent. In certain embodiments, the mammal's symptoms (such as flushing, nausea, fever, or other maladies associated with cancerous disease) are alleviated.

In certain embodiments of the methods described above, the composition is administered intraveneously, orally, subcutaneously, or as an aerosol. In certain embodiments of the methods described above, the composition is administered intraveneously at a dosage of 5-200 micromols/kg/day of XTPP, such as 20-130 micromols/kg/day of XTPP. In certain embodiments of the methods described above, the composition is administered orally at a dosage of 5-200 micromols/kg/day of XTPP, such as 20-130 micromols/kg/day of XTPP.

The present invention provides a method for treating cancer in a subject, comprising administering to the subject an effective amount of XTPP and an inhibitor or inhibitors of hydroperoxide metabolism and/or an inhibitor of glutathione metabolism so as to treat the cancer.

In certain embodiments, the present invention provides a composition comprising a decyl-triphenylphosphonium (DTPP) or a pharmaceutically acceptable salt thereof, and an inhibitor of hydroperoxide metabolism for use in the treatment of cancer, wherein the composition is to be administered to a patient that has cancer or is at risk for developing cancer.

In certain embodiments, the present invention provides a composition comprising a decyl-triphenylphosphonium (DTPP) or a pharmaceutically acceptable salt thereof, and an inhibitor of hydroperoxide metabolism for use in inducing cellular apoptosis of a cancerous cell, wherein the composition is to be administered to a patient that has cancer or is at risk for developing cancer.

BRIEF DESCRIPTION OF THE DRAWINGS

FIG. 16: The fraction of Aldehyde dehydrogenase activity positive (ALDH+) cancer cells (also known as early progenitor cancer stem cells) is decreased in SUM159 human breast cancer cells treated with inhibitors of glutathione and thioredoxin metabolism (BSO, AUR, respectively) combined with DTPP. Asynchronously growing cultures of SUM159 were incubated with 100 µM BSO and/or 1 µM DTPP for 24 hours in HMEC media. 500 nM AUR were added into cell culture 15 minutes before the assay. Monolayer cultures were harvested and trypsinized, washed once with PBS and labeled 40 minutes in PBS at 37° C. with BAAA (1 µmol/1 per 1 x $10^6$ cells). The negative controls were also added with 50mmol/L diethylaminobenzaldehyde (DEAB). After labeling, Hochest dye for viability assay was added and then kept on ice. Each sample was then analyzed for the ALDH positive cell percentage of 100,000 cells by flow cytometry. Errors represent Mean ±1 SD of 3 samples from two separate experiments (n=9), * p <0.05 as compared to Control. These results show the ability of the combination of DTTP with inhibitors of glutathione and thioredoxin mediated hydroperoxide metabolism to cause a reduction in the cancer stem cell fraction of the breast cancer cell population. Since cancer stem cells are believed to be the fraction of cells capable of regrowth and subsequent treatment failure, this result suggests that this strategy has efficacy in treating human cancers.

FIG. 17: Measurement of AUR, DTPP and NAC interactions with Ellman's reagent. Different concentrations (0.01 mM-10 mM) of NAC, DTPP and AUR solutions were prepared. Equal moles of NAC, DTPP or AUR from each concentration were added together along with DTNB [5,5' - dithio-bis- (2-nitrobenzoic acid)], respectively. For each combination, the same moles of single agents were also added with DTNB. DMSO was added into NAC alone solution to maintain the same DMSO level in NAC+DTPP/AUR combinations. The absorbance of DTNB's reduction to 2-nitro-5-thiobenzoate (TNB) was then measured spectrophotometrically at 412 nM. For NAC and AUR interaction test, sample tubes were incubated in a 4%, 37° C. incubator for at least 1h. For NAC and DTPP interaction test, sample tubes were incubated in a 4%, 37° C. incubator for 24h. The results show that both NAC and AUR were capable of reducing DTNB confirming their reactivity with disulfide containing compounds like DTNB.

FIG. 18: Intracellular GSH&GSSG measured in BSO, DTPP, and AUR exposed SUM159 cells. Asynchronously growing cultures of SUM159 were plated and treated as described in FIG. 1. Cells were harvested and scraped in PBS at 4° C. Whole cell homogenates were used for biochemical analysis of total GSH & GSSG levels. Errors represent Mean ±1 SD of 4 samples from two separate experiments (n=4). The results show that BSO was capable of depleting GSH, and that combinations of DTTP with these reagents (as well as DTTP alone) were capable of inducing oxidative stress in cancer cells as indicated by increases in % GSSG.

DETAILED DESCRIPTION

Figure 1A:
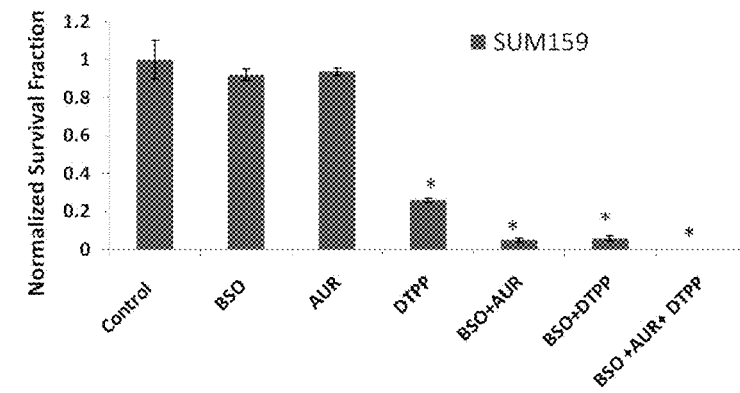
FIGS. 1A-D: BSO, DTPP and AUR treated SUM159, MDA-MB231 and HMEC Clonogenic survival. In Panel A (SUM 159), B (MDA-MB231) and C(HMEC), 150,000 cells/dish SUM159 or MDA-MB231 and 300,000 cells/dish were plated in 60 mm tissue culture dishes. After 48 hours, cells were given fresh complete HMECs media and treated with 100 μM BSO+/1 μM DTPP for 24 hours. 500 nM AUR were added 15 mins before the trypsinization of cells for clonogenic survival assay. In panel A-C, The error bars represent mean±1 SD of n=1 treatment dishes done in 3 separate experiments where each treatment dish was used to prepare 6-10 replicate cloning dishes for analysis. *p<0.001 as compared to Control. These results show that these drug combinations were selectively cytotoxic to the reproductive integrity of cancer (Sum159 and MDA-MB231) vs. normal cells (HMEC). This data supports the claim that these drug combinations may be effective at treating cancer cells while sparing normal tissue. Panel 1D shows in vivo treatment with Au, BSO and DTPP alone and in combinations results in a decrease of ALDH+cells in Sum 159 xenografts. Mice growing Sum159 xenograft tumors were treated with 100 μM DTPP in drinking water for 2 weeks followed by i.p. injections of BSO 675 mg/kg followed in 2 hrs with Au 2.7 mg/kg. The day following injections tumors were harvested, digested and stained for ALDH positive cells. Each bar represents an average of at least three tumors. Error bars are SEM. *p<0.05 vs. control.

It is becoming increasing evident that cancer cells relative to normal cells have fundamental differences in mitochondrial oxidative metabolism. The inventors have exploited this invention to develop novel combined modality cancer therapies that would selectively enhance metabolic oxidative stress-induced cell killing in cancer vs. normal cells (Aykin-Burns N, Ahmad I M, Zhu Y, Oberley L W, and Spitz D R: Increased levels of superoxide and hydrogen peroxide mediate the differential susceptibility of cancer cells vs. normal cells to glucose deprivation. Biochem. J. 2009; 418:29-37. PMID: 189376440).

It has been discovered that decyl-triphenylphosphonium (DTPP) combined with inhibitors of hydroperoxide metabolism selectively enhances human cancer cell killing via oxidative stress, relative to normal human cells. Breast cancer cells have been hypothesized to produce increased steady-state levels of reactive oxygen species (ROS) from mitochondrial metabolism (relative to normal cells) that mediate increased susceptibility to agents which induce oxidative stress (Aykin-Burns N, Ahmad I M, Zhu Y, Oberley L W, and Spitz D R: Increased levels of superoxide and hydrogen peroxide mediate the differential susceptibility of cancer cells vs. normal cells to glucose deprivation. Biochem. J. 2009; 418:29-37. PMID: 189376440). However, relatively little is known about the therapeutic significance of these observations. To determine if an agent that increases the mitochondrial ROS combined with inhibitor of hydroperoxide metabolism could enhance the cytotoxicity to preferentially kill breast cancer cells (relative to breast normal cells), DTPP (1 µM), a lipophilic cation that localizes to cancer cell mitochondria, was utilized in combination with inhibitors of hydroperoxide metabolism [i.e., L-buthionine-S,R-sulfoximine, BSO (100 µM), Auranofin (S-triethylphosphinegold(I)-2,3,4,6-tetra-O-acetyl-1-thio-b-Dglucopyranoside), AUR (500 nM)] to treat breast cancer cells in vitro. Results clearly showed that BSO+DTPP treatment could induce at least additive (and possibly greater than additive) clonogenic cell killing in MDA-MB231 and SUM159 human breast cancer cells, that was significantly less toxicity than was seen in normal human mammary epithelial cells. Furthermore, AUR (500 nM) could further sensitize cancer cells to the cytotoxicity of BSO±DTPP. These treatments could also significantly decrease cancer cell expression of aldehyde dehydrogenase (ALDH), a marker of cancer stem cells. Furthermore, increases in parameters indicative of oxidative stress, including steady-state levels of $CDCFH_2$, and MitoSOX oxidation, were also observed in BSO, DTPP and AUR treated human breast cancer cells, relative to normal cells. N-acetylcysteine, a non-specific thiol antioxidant, and PEG-SOD and PEG-CAT could rescue toxicity of BSO, DTPP and AUR exposed SUM159 and MDA-MB231 cells. These results support the hypothesis that inhibiting hydroperoxide metabolism while increasing steady-state levels of mitochondrial ROS with DTPP in breast cancer cells could selectively kill breast cancer, relative to normal breast epithelial cells by inducing oxidative stress. Furthermore these results suggest that this biochemical rationale might be used to develop novel cancer therapies that could be broadly applicable in human cancer therapy.

Triphenylphosphonium Salts

Triphenylphosphonium (TPP) salts can be reacted with alcohols, alkyl halides, and carboxylic acids, which allow them to be used as starting materials for the synthesis of a large variety of chemical derivatives, e.g., XTPP agents. Charged molecules generally cannot pass through cell membranes without the assistance of transporter proteins because of the large activation energies need to remove of associated water molecules. In the TPP molecules, however, the charge is distributed across the large lipophilic portion of the phosphonium ion, which significantly lowers this energy requirement, and allows the TPP to pass through lipid membranes. The phosphonium salts accumulate in mitochondria due to the relatively highly negative potential inside the mitochondrial matrix. The compositions of the present invention utilize XTPP agents that have activity in treating cancer cells, in that the XTPP agents preferentially localize to cancer cells, as compared to the comparable normal cells because cancer cells are often characterized by abnormal mitochondrial oxidative metabolism (Aykin-Burns N, Ahmad I M, Zhu Y, Oberley L W, and Spitz D R: Increased levels of superoxide and hydrogen peroxide mediate the differential susceptibility of cancer cells vs. normal cells to glucose deprivation. Biochem. J. 2009; 418:29-37. PMID: 189376440) and altered mitochondrial membrane potential (Chen L B: Mitochondrial membrane potential in living cells, Ann. Rev. Cell Biol. 1988; 4:155-81), relative to normal cells.

In certain embodiments, the XTPP agent comprises a triphenylphosphonium (TPP) molecule or a pharmaceutically acceptable salt thereof. As used herein, the term triphenylphosphonium is any molecule containing a triphenylphosphine cation ($^+$PPh$_3$) moiety.

In certain embodiments, the XTPP agent is $^+$PPh$_3$-X—R; wherein:

X is a (C$_2$-C$_{50}$)alkyl;

R is H, N$_3$, triazole optionally substituted with one or more (e.g. 1 or 2) (C$_4$-C$_8$)alkyl or quinone optionally substituted one or more (e.g. 1, 2 or 3) (C$_1$-C$_6$)alkyl or —O(C$_1$-C$_6$)alkyl; and Y is a counterion;

or a pharmaceutically acceptable salt thereof.

As used herein, the term alkyl is defined as a straight or branched hydrocarbon. For example, an alkyl group can have 2 to 50 carbon atoms (i.e, (C$_2$-C$_{50}$)alkyl), 1 to 10 carbon atoms (i.e., (C$_1$-C$_{10}$)alkyl), 1 to 8 carbon atoms (i.e., (C$_1$-C$_8$)alkyl) or 1 to 6 carbon atoms (i.e., (C$_1$-C$_6$ alkyl). Examples of suitable alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butly, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$) and decyl (—(CH$_2$)$_9$CH$_3$).

In certain embodiments, R imparts hydrophilicity or reactive properties cytotoxic to cancer cells.

In certain embodiments R is:

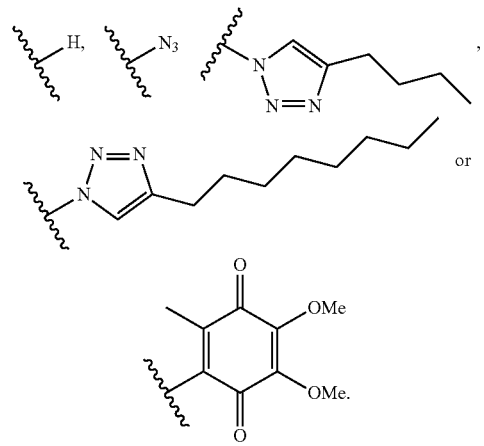

In certain embodiments, X is —(CH$_2$)$_{10}$—.

In certain embodiments, the XTPP agent that increases reactive oxygen species (ROS) levels in cancer cell mitochondria is;

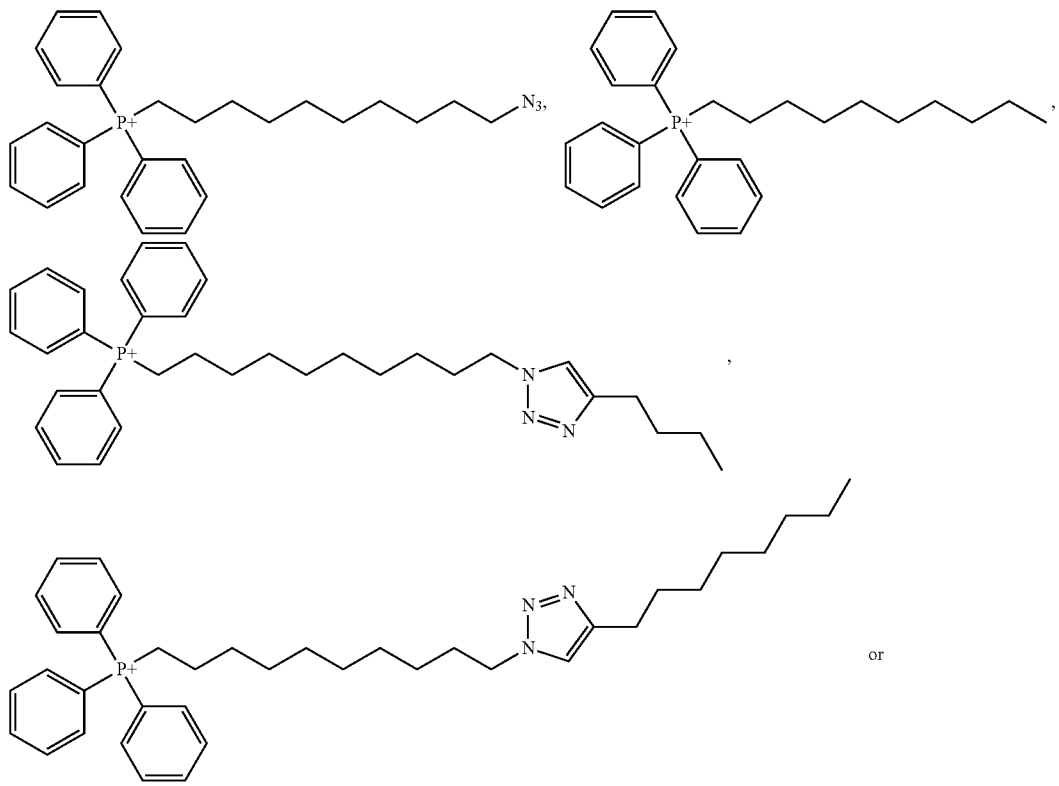

-continued

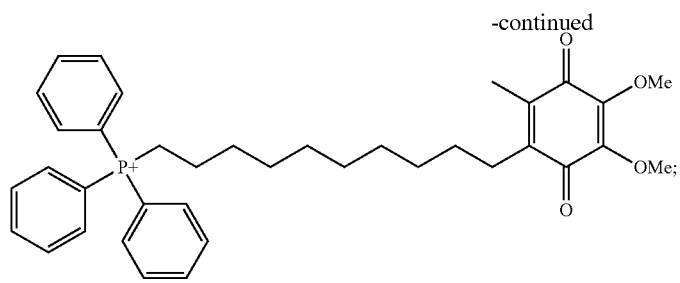

or a pharmaceutically acceptable salt thereof.

Inhibitors of Hydroperoxide Metabolism

The inventors discovered that the addition of inhibitors of hydroperoxide metabolism via glutathione and/or thioredoxin dependent pathways to a composition including an XTPP agent, that selectively enhances clonogenic cell killing via oxidative stress and accumulation of oxidative damage to critical biomolecules (i.e., proteins, lipids, and nucleic acids), in human cancer cells, relative to normal human cells. This selective property of the drug combination(s) for clonogenically inactivating cancer cells is the result of inherent differences in pro-oxidant levels generated in cancer vs. normal cells as by products of oxidative and reductive metabolism necessary for maintenance of cell viability and reproduction. More specifically, cancer cells (relative to normal cells) demonstrate increased levels of reactive oxygen species (i.e., superoxide, hydroperoxides, and reactive species derived from the oxidation of proteins, lipids, and nucleic acids) due to fundamental differences in cancer vs. normal cell metabolism of oxygen. The addition of these inhibitors of hydroperoxide metabolism to a composition including XTPP also enhances the efficacy of conventional radiation and chemotherapies used to treat human cancers. In certain embodiments, the inhibitors of hydroperoxide metabolism are L-buthionine-[S,R]-sulfoximine (BSO), (S-triethylphosphinegold(I)-2,3,4,6-tetra-O-acetyl-1-thio-b-Dglucopyranoside Auranofin (AUR), or a combination of BSO and AUR. BSO and AUR or a combination of these two compounds are employed to inhibit thiol mediated hydroperoxide metabolism by both glutathione- and thioredoxin-dependent pathways which causes oxidative stress and accumulation of oxidative damage to critical biomolecules (i.e., proteins, lipids, and nucleic acids) in cancer versus normal cells resulting in cancer cell specific clonogenic cell killing in both early progenitor cancer stem cells as well as all other cancer cells capable of continued mitotic activity. Other compounds that could also be used for this purpose include inhibitors of catalase (i.e., 3-aminotriazole), inhibitors of glucose metabolism (i.e., bromopyruvate and 2-deoxyglucose), inhibitors of peroxiredoxins, inhibitors of glutathione peroxidases, inhibitors of dehydrogenase enzymes that regenerate NADPH, inhibitors of thioredoxin reductase, inhibitors of glutathione reductase, inhibitors of glutathione transferases, and inhibitors of transcription factors as well as signal transduction proteins that regulate thiol mediated hydroperoxide metabolism (i.e., Nrf-2, AP-1, NFkB, AKT, ERK1/2, p38, EGFR, and IGFR). Another strategy to enhance the efficacy of a composition including XTPP with inhibitors of hydroperoxide metabolism would include feeding patients diets high in respiratory directed substrates including ketogenic diets, Atkins style diets, and pharmacological doses of IV vitamin C which would be expected to further enhance the differential pro-duction of pro-oxidants mentioned previously in cancer vs. normal tissues.

Compositions to Kill Cancer Cells via Oxidative Stress

The present invention provides compositions to kill cancer cells via oxidative stress. In certain embodiments XTPP and inhibitors of hydroperoxide metabolism are combined into a single composition. In other embodiments, the two components are administered individually or sequentially. In some embodiments of the invention, the effective amount of the XTPP and the inhibitors of hydroperoxide metabolism (e.g., that is administered to the subject) does not significantly affect the viability of comparable normal cells. For example, the effective amount causes the killing of less than 100% (e.g., less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, or less than about 5%) of the comparable normal cells. For example, the composition could kill breast cancer cells present in a mammal, but kill fewer than 100% of the normal breast cells, e.g., only 5% of the normal breast cells.

Methods of Treatment

The terms "treat" and "treatment" refer to both therapeutic treatment and prophylactic or preventative measures, wherein the object is to prevent or decrease an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The XTPP and inhibitors of hydroperoxide metabolism may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal.

The dosage of the XTPP and inhibitors of hydroperoxide metabolism will vary depending on age, weight, and condition of the subject. Treatment may be initiated with small dosages containing less than optimal doses, and increased until a desired, or even an optimal effect under the circumstances, is reached. In general, the dosage is about 1 µg/kg up to about 100 µg/kg body weight, e.g., about 2 µg/kg to about µg/kg body weight of the subject, e.g., about 8 µg/kg to about 35 µg/kg body weight of the subject. Higher or lower doses, however, are also contemplated and are, therefore, within the confines of this invention. A medical practitioner may prescribe a small dose and observe the effect on the subject's symptoms. Thereafter, he/she may increase the dose if suitable. In general, the XTPP and inhibitors of hydroperoxide metabolism are administered at a concentration that will afford effective results without causing any unduly harmful or deleterious side effects, and may be administered either as a single unit dose, or if desired in convenient subunits administered at suitable times.

A pharmaceutical composition of the invention is formulated to be compatible with its intended route of administration. For example, the therapeutic agent may be introduced directly into the cancer of interest via direct injection. Additionally, examples of routes of administration include oral, parenteral, e.g., intravenous, slow infusion, intradermal, subcutaneous, oral (e.g., ingestion or inhalation), transdermal (topical), transmucosal, and rectal administration. Such compositions typically comprise the XTPP and inhibitors of hydroperoxide metabolism and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art.

Solutions or suspensions can include the following components: a sterile diluent such as water for injection, saline solution (e.g., phosphate buffered saline (PBS)), fixed oils, a polyol (for example, glycerol, propylene glycol, and liquid polyetheylene glycol, and the like), glycerine, or other synthetic solvents; antibacterial and antifungal agents such as parabens, chlorobutanol, phenol, ascorbic acid, thimerosal, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol or sorbitol, and sodium chloride in the composition. Prolonged administration of the injectable compositions can be brought about by including an agent that delays absorption. Such agents include, for example, aluminum monostearate and gelatin. The parenteral preparation can be enclosed in ampules, disposable syringes, or multiple dose vials made of glass or plastic.

It may be advantageous to formulate compositions in dosage unit form for ease of administration and uniformity of dosage. Dosage unit form as used herein refers to physically discrete units suited as unitary dosages for an individual to be treated; each unit containing a predetermined quantity of active compound calculated to produce the desired therapeutic effect in association with the required pharmaceutical carrier. The dosage unit forms of the invention are dependent upon the amount of a compound necessary to produce the desired effect(s). The amount of a compound necessary can be formulated in a single dose, or can be formulated in multiple dosage units. Treatment may require a one-time dose, or may require repeated doses.

The invention will now be illustrated by the following non-limiting Example.

EXAMPLE 1

Decyl-Triphenylphosphonium Combined with Inhibitors of Hydroperoxide Metabolism Enhances Breast Cancer Cell Killing Via Oxidative Stress It has been known for more than 80 years that cancer cells, relative to normal cells showed altered oxidative metabolism, where cancer cells exhibited higher rate of glycolysis and pentose phosphate cycle activity. It was first thought that increased glycolysis derives from fast tumor growth, which was thought to merely represent a byproduct of oncogenic transformation. However, recent research suggests that cancer cells have higher steady-state levels of superoxide and peroxides compared to normal cells. Furthermore, in addition to providing energy for cells, glycolysis and the pentose phosphate cycle also produce pyruvate and NADPH to provide reducing equivalents for hydroperoxide metabolism. Moreover, previous studies showed that glucose deprivation could preferentially kill cancer cells, relative to normal cells. Given the observations above, it is possible to hypothesize that cancer cells (relative to normal cells) may increase glucose metabolism as a compensatory mechanism to protect against intracellular ROS. If this is the case, then inhibiting glucose or hydroperoxide metabolism while forcing cells to derive energy from respiration should preferentially kill cancer cells, relative to normal cells.

To take advantage of this hypothesis, targeting hydroperoxide metabolism has been explored previously as a therapeutic approach. Of all the inhibitors of hydroperoxide metabolism that were evaluated, BSO is the one that has been best characterized in animal model studies and human clinical trials. BSO is a Glutathione (GSH) synthesis inhibitor. It can inhibit glutamate cysteine ligase (GCL) activity, therefore inhibiting GSH synthesis and decreasing the GSH level. It is well known that GSH and GSH dependent enzymes play a very important role in hydroperoxides metabolism, and therefore decreasing GSH level by BSO could significantly increase the oxidative stress in cancer cells and increase their susceptibility compared to normal cells. Nonetheless, the implementation of BSO as single anticancer agent in vivo has been a disappointment. Recent research suggested that when BSO was administered as a single anticancer agent, it did not show significant inhibition on tumor growth (Simons, A. L.; Parsons, A. D.; Foster, K. A.; Orcutt, K. P.; Fath, M. A.; Spitz, D. R. Inhibition of glutathione and thioredoxin metabolism enhances sensitivity to perifosine in head and neck cancer cells. *J Oncol* 2009: 519563; 2009). However, more recently the inventors have discovered that simultaneous inhibition of both glutathione and thioredoxin dependent hydroperoxide metabolism with BSO and AUR was exceedingly effective at killing as well as chemo-sensitizing lung cancer cells to the chemotherapy agent, carboplatin (Fath M A, Ahmed I M, Smith C J, Spence J, and Spitz D R: Enhancement of carboplatin-mediated lung cancer cell killing by simultaneous disruption of glutathione and thioredoxin metabolism. *Clin. Cancer Res.* 2011; in revision). This is believed to be because the glutathione and thioredoxin dependent hydroperoxide metabolic pathways may have several redundancies necessitating the inhibition of both for maximal effects in cancer cells. It has been known for a long time that cancer cells have more versatility than normal cells, and therefore the stress produced by a single agent might cause cancer cells to compensate by other pathways to reverse its cytotoxicity effects. Therefore, in order to increase the susceptibility of cancer cells, relative to normal cells and design optimal drug treatment, a multi-targeted approach to anti-cancer drug development should be involved.

Mitochondria might be a highly promising, relatively undervalued anti-cancer target. Research by the inventors demonstrated that mitochondrial produced ROS significantly contribute to the differential susceptibility of cancer and normal cells to glucose deprivation-induced cytotoxicity and oxidative stress (Aykin-Burns N, Ahmad I M, Zhu Y, Oberley L, and Spitz D R. Increased levels of superoxide and hydrogen peroxide mediate the differential susceptibility of cancer cells vs. normal cells to glucose deprivation. Biochem J. 2009; 418:29-37. PMID: 18937644 PMCID: PMC2678564). More data also suggested that using mitochondrial electron transport chain blockers could also enhance glucose-deprivation induced oxidative stress and cell killing in human cancer cells (Ahmad I M, Aykin-Burns N, Sim J E, Walsh S A, Higashikubo R, Buettner G R, Venkataraman S, Mackey M A, Flanagan S, Oberley L W, and Spitz D R: Mitochondrial $O2.^{31}$ $^{and}$ $^{H}2O2$ mediate glucose deprivation-induced cytotoxicity and oxidative stress in human cancer cells. J. Biol. Chem. 2005; 280(6): 4254-4263. PMID: 15561720; Fath M A, Diers A R, Aykin-Burns N, Simons A L, Hua L, and Spitz D R: Mitochondrial electron transport chain blockers enhance 2-deoxy-D-glucose induced oxidative stress and cell killing in human colon carcinoma cells. Cancer Biol Ther 2009; 8(13):1228-36. PMID: 19411865 PMCID: PMC2771689). However, it has not been established to use mitochondrial targeted compounds that selectively increase pro-oxidant production in cancer cells as therapeutic agents to treat cancers. Furthermore, thiol metabolism has been suggested to be an integral component of the intracellular metabolic hydroperoxide detoxification pathways. Therefore, it is logical to hypothesize that by increasing the steady-state levels of ROS (i.e. $O_2.^-$, $H_2O_2$) from mitochondrial metabolism in cancer cells (relative to normal cells) would be selectively sensitized to oxidative stress and cytotoxicity when using inhibitors of hydroperoxide metabolism that disrupt thiol metabolism.

In order to test this hypothesis, a membrane-permeable cation, Decyl-Triphenylphosphonium (DTPP) was utilized in this study. DTPP is the lipophilic cation which accumulates into the cell driven by the plasma membrane potential and then accumulates further into mitochondria. It was suggested that the extensive accumulation of lipophilic cations within isolated mitochondria can disrupt membrane integrity, respiration, ATP synthesis and might increase ROS production. It has also been known that DTPP-analogous compounds like tetraphenylphosphonium chloride inhibit the growth of cell lines derived from a wide variety of carcinomas (breast, colon, pancreas, bladder, and hypopharynx) relative to untransformed cell lines in vitro. However, very little is known about the mechanism of DTPP compounds induced cytotoxicity and its anti-cancer effects. Here, when MDA-MB231 and SUM159 human breast cancer cells were treated with DTPP alone or combined with inhibitors of hydroperoxide metabolism (BSO and AUR), results clearly showed that DTPP treatment could lead to increases in parameters indicative of oxidative stress (i.e. Mitochondrial $O_2.^-$, $H_2O_2$ and GSSG) and significantly enhanced cancer cell clonogenic cell killing in the presence of BSO, relative to normal human mammary epithelial cells (HMEC). We further tested the working hypothesis that the alkyl carbon chain has reactive significance in the induced cytotoxic effect by control experiments in which a bis-decylTPP compound was synthesized and used for similar clonogenic cell killing assays. In addition, an azido-DTPP compound was synthesized and used for similar clonogenic assays to determine the potential for additional structure activity relationship potential that results from modifications to the DTPP alkyl carbon chain. An inhibitor of thioredoxin reductase, AUR, further sensitized human breast cancer cells to the toxicity of BSO+DTPP, which almost decreased the cancer cell cloning efficiency to zero. The same drug treatments also significantly diminished the cancer stem cell (CSC) population, a sub-component that retains key stem cell properties and drives tumorigenesis and malignancy, by determining the ALDH activity of SUM159 human breast cancer cells. Furthermore, a nonspecific thiol antioxidant (N-acetylcysteine NAC) inhibited the clonogenic cell killing induced by BSO, DTPP and AUR treatments. These results provide strong evidence to support the hypothesis that DTPP could enhance the cancer cell killing mediated by BSO and AUR and further contribute to the differential susceptibility of normal vs. breast cancer cells by selectively increasing mitochondrial ROS and oxidative stress. Considering that these combinations were also efficient in limiting CSC in human breast cancer cells, these findings provide a novel biochemical rationale of multi-targeted approach to anti-breast cancer drug development by inhibiting hydroperoxide metabolism combined with mitochondrial targeted agents that enhance pro-oxidant levels.

Materials and Methods:

General chemistry: All solvents and reagents were used as received unless otherwise stated and were ACS grade or higher. Water was 0.22 mm filtered deionized 18 mΩ milliQ Advantage purification system processed (Millpore, Billerica, Mass. USA).

Synthesis of bis-TPP: Bis-TPP was synthesized by refluxing triphenylphosphine (0.8 g, 2.0 mMol) with a 10-fold excess of 1,10-dibromodecane (1.0 g, 20.0 mMol) in 10 mL benzene for 3 days at 80° C. The final product was purified by silica gel chromatography using the following solvents: (50% hexanes/50% ethyl acetate; 100% ethyl acetate; 10% methanol/90% ethyl acetate; 50% methanol/50% ethyl acetate; and 100% methanol). Fractions collected were analyzed using thin layer chromatography. Mass spectroscopy confirmed final product mass (observed 664, calculated 664.84).

Synthesis of azido-decylTPP: Azido-decylTPP was synthesized by refluxing triphenylphosphine (0.5 g, 2.0 mMol) (AlphaAesar®, L02502, Ward Hill, Mass.) with a 25-fold excess of 1,10-dibromodecane (10.5 g, 50.0 mMol) (AlphaAesar®, L07383, Ward Hill, Mass.) in 10 mL benzene for 24 hrs. at 80° C. yielding a (10-bromodecyl)triphenylphosphonium intermediate. The intermediate (0.77 g, 1.6 mMol) was refluxed with a 5-fold excess of $NaN_3$ (0.52 g, 8.0 mMol) in a 30 mL 1:1 mixture of EtOH and water for 24 hrs. at 80° C. yielding (10-azidodecyl)triphenylphosphonium. The final product was purified by silica gel chromatography using the following solvents: (50% hexanes/50% ethyl acetate; 100% ethyl acetate; 10% methanol/90% ethyl acetate; 50% methanol/50% ethyl acetate; and 100% methanol). Fractions collected were analyzed using thin layer chromatography. Mass spectroscopy confirmed final product mass (observed 444.23, calculated 444.57). Bis-TPP was synthesized by refluxing triphenylphosphine with a 10 fold excess of 1, 10-dibromodecane in 10 mL benzene for 3 days at 80° C. Mass spectroscopy confirmed mass of the final products (azido-decylTPP MW 444.23; bis-TPP MW 664).

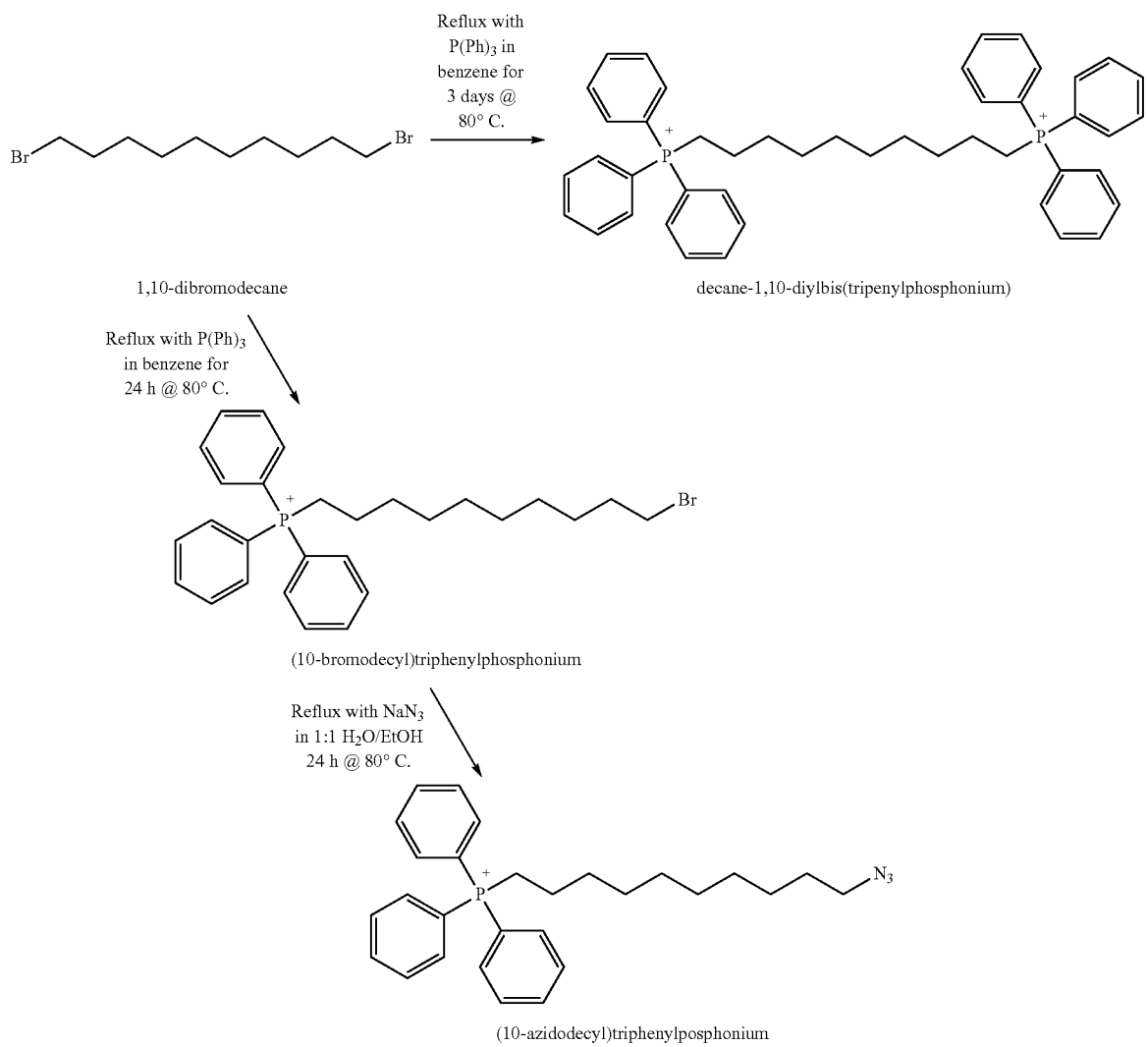

Cells and Culture Conditions: MDA-MB231 and SUM159 human breast cancer cells were obtained from the American Type Culture Collection (Manassas, Va., USA). MDA-MB231 cells were maintained in RPMI 1640 medium supplemented with 10% fetal bovine serum (FBS; Hyclone, Logan, Utah, USA). SUM159 cells were maintained in Ham's F-12 medium (Gibco Invitrogen, Carlsbad, Calif., America) containing 10 mM HEPES (Gibco Invitrogen, Carlsbad, Calif., USA), 10 ng/ml insulin (Sigma, St. Louis, Mo.), 1 mg/ml hydrocortisone (Sigma, St. Louis, Mo.), and 5% fetal bovine serum (FBS; Hyclone, Logan, Utah, USA). Normal (non-immortalized) human mammary epithelial cells (HMEC) were purchased from Clonetics (East Rutherford, N.J., USA) and maintained in MEBM serum free medium (Lonza Group Ltd, Switzerland) with additives [recombinant human epidermal growth factor (rhEGF), bovine pituitary extract (BPE), recombinant human insulin, hydrocortisone, and gentamicin]. All the cell cultures were maintained in humidified 37° C. incubator with 5% $CO_2$ and 4% $O_2$. All experiments were done using exponentially growing cell cultures at 50-70% confluence. DMSO and PBS were used as the vehicle control in all experiments.

Drug Treatment: BSO, NAC, Polyethylene glycol (PEG), polyethylene glycol-catalase (PEG-CAT), and polyethylene glycol-superoxide dismutase (PEG-SOD) were obtained from Sigma Chemical Co. (St. Louis, Mo., USA). Auranofin (AUR) was obtained from ICN Biochemicals (Aurora, Ohio). Decyl-triphenylphosphonium (DTPP) was obtained from Dr. Michael P. Murphy at Medical Research Council Mitochondrial Biology Unit, Cambridge CB2 0XY, UK. All drugs were used without further purification. Drugs were added to cells at the final concentrations of 100 μM BSO, 1 μM DTPP, 500 nM AUR, 20 mM NAC, 18 μM PEG, 100 U/ml PEG-CAT and 100 U/ml PEG-SOD. Stock solutions of 0.01 M BSO, 5 U/μl PEG-CAT and 5 U/μl PEG-SOD were dissolved in PBS and the required volume was added directly to the cells to achieve the desired final concentration (PEG alone at the same concentration (18 μM) was added as the control). Stock solutions of 1 mM TPP and 1 mM AUR were dissolved in dimethyl sulfoxide (DMSO), respectively, with the final concentration of 0.1% in the medium (vehicle-alone controls were also included). Stock solutions of 1 M NAC (in 1 M sodium bicarbonate, pH 7.4) were added directly to the cell cultures to obtain the desired concentration.

Clonogenic cell survival: To determine whether the DTPP exposure alters the cell proliferation in MDA-MB231, SUM159 and HMECs, 150,000 cells/dish of MDA-MB231 and SUM159 cells, and 300,000 cells/dish HMECs were plated in 60 mm tissue culture dishes. After 48 hours, at 24 hours prior to each clonogenic survival experiment, media in all the dishes were changed to HMECs media and then treated with 100 μM BSO and 1 μM DTPP for 24 h. Cells were treated with AUR for 15 minutes prior to each clonogenic survival experiment. Attached and floating cells in the experimental dishes were collected after trypsinization with 1× trypsin-EDTA (CellGro, Herndon, Va., USA), centrifuged, resuspended in fresh media, and counted using a Coulter counter. Cells were re-plated using appropriate dilutions in their own media and clones were allowed to grow for 14 days in their regular growth media in the presence of 0.1% gentamycin. Cells were then fixed with 70% ethanol and stained with Coomassie blue and colonies of more than 50 cells counted and utilized to calculate clonogenic survival as described (Puck, T. T.; Morkovin, D.; Marcus, P. I.; Cieciura, S. J. Action of x-rays on mammalian cells. II. Survival curves of cells from normal human tissues. *J Exp Med* 106:485-500; 1957; Spitz, D. R.; Malcolm, R. R.; Roberts, R. J. Cytotoxicity and metabolism of 4-hydroxy-2-nonenal and 2-nonenal in H2O2-resistant cell lines. Do aldehydic by-products of lipid peroxidation contribute to oxidative stress? *Biochem J* 267:453-459; 1990).

Survival experiments using PEG-CAT/PEG-CuZnSOD and NAC Treatments: In order to test for a possible causal relationship between the biological effects of BSO, DTPP and AUR treated breast cancer cells, as well as the observed increases in parameters indicative of oxidative stress, a clonogenic assay with BSO DTPP and AUR and antioxidant treatments was performed. Cells were plated at a density of 150,000 cells/60 mm dish as described earlier in clonogenic survival experiment. After 48 hours. PEG alone (18 μM) or PEG-CAT combined with PEG-CuZnSOD (100 U/mL each) or NAC (20 mM) were added into the cell culture media on SUM159 or MDA-MB231 cells. 1 hour later after antioxidant addition, cells also received BSO, DTPP and treatment for 24 hour. Prior to each clonogenic survival experiment, AUR was added for 15 minutes. Then, cells were trypsinized, counted, and re-plated in complete control media using appropriate dilutions, and clonogenic survival evaluated.

Estimation of Cancer stem cell fractions using the Aldefluor assay: The ALDEFLUOR kit (StemCell Technologies, Durham, N.C., USA) was used to determine the subpopulation of cancer cells with a high ALDH enzymatic activity. SUM159 human breast cancer cells were plated and treated as described earlier in clonogenic survival experiment. After the exposure, the cells were trypsinized and washed with PBS once then re-suspended in ALDEFLUOR assay buffer containing ALDH substrate (BAAA, 1 μmol/l per $1 \times 10^6$ cells) and incubated for 40 minutes at 37° C. As negative control, for each sample of cells an aliquot was treated with 50 mmol/L diethylaminobenzaldehyde (DEAB), a specific ALDH inhibitor. In order to sort out non-viable cells, each sample received 4 μg/ml of Hoechst 33258 (Molecular Probes, Invitrogen). Cells were filtered through 35 mm mesh and kept on ice until analysis. Samples were analyzed by using a Becton Dickinson LSR II with 355 nm, 488 nm, and 633 nm lasers. (Becton Dickinson Immunocytometry System, INC., Mountain View, Calif.). The ALDH positive cells of 100,000 cells were determined by using the sorting gate established with DEAB negative control and Hochest viability control. The ALDH positive cells were represented by percentage of total 100,000 cell events.

Estimation of intracellular superoxide levels using Dihydroethidium (DHE) oxidation: Steady-state levels of superoxide were estimated using the fluorescent dyes, dihydroethidium (DHE) purchased from Molecular Probes (Eugene, Oreg.). Cells were plated and treated for as described earlier. On day 6, the cells were trypsinized and washed with 5 mM/L pyruvate containing PBS once then labeled with DHE (10 μM, in 0.1% DMSO, 40 min) at 37° C. After labeling, cells were kept on ice. Samples were analyzed using a FACScan flowcytometer (Becton Dickinson Immunocytometry System, INC., Mountain View, Calif.) (excitation 488 nm, emission 585 nm band-pass filter). The mean fluorescence intensity (MFI) of 10,000 cells was analyzed in each sample and corrected for autofluorescence from unlabeled cells. The MFI data was normalized to control levels.

MitoSOX™ red oxidation to estimate mitochondrial superoxide production: To determine if DTPP can alter steady-state levels of superoxide originating from mitochondria in SUM159, MDA-MB231 and HMEC cells, the cationic superoxide sensitive dye, MitoSOX™red (Molecular Probes), was used. Cells were plated and treated as described earlier in clonogenic survival experiment. After the exposure, cells were trypsinized and washed with 5 mM/L pyruvate containing PBS once then labeled with MitoSOX™red (2 μM, in 0.1% DMSO, 20 minutes) at 37° C. After labeling, cells were kept on ice. Samples were analyzed using a FACScan flowcytometer (Becton Dickinson Immunocytometry System, INC., Mountain View, Calif.) (excitation 488 nm, emission 585 nm band-pass filter). The mean fluorescence intensity of 10,000 cells was analyzed in each sample and corrected for autofluorescence from unlabeled cells. The MFI data was normalized to control levels.

Measurement of Intracellular Hydroperoxides: Steady-state levels of hydroperoxides were estimated using the oxidation sensitive {5-(and-6)-carboxy-2',7'-dichlorodihydrofluorescein diacetate, ($CDCFH_2$)} and oxidation-insensitive {5-(and-6)-carboxy-2',7'-dichlorofluorescein diacetate, (CDCF)} fluorescent dyes purchased from Molecular Probes. Cells were plated and treated with BSO, DTPP and AUR as described above. After the exposure, cells were trypsinized and washed with PBS once then labeled with $CDCFH_2$ or CDCF (10 μg/mL, in 0.1% DMSO, 15 minutes) at 37° C. After labeling, cells were kept on ice. Samples were analyzed using a FACScan flowcytometer (Becton Dickinson Immuno-cytometry System, INC., Mountain View, Calif.) (excitation 488 nm, emission 530 nm band-pass filter). The MFI of 10,000 cells was analyzed in each sample and corrected for autofluorescence from unlabeled cells. The MFI data was normalized to control levels.

Glutathione analysis: SUM159 Cells were plated and treated with BSO, DTPP and AUR as described above. When cells were grown to 70-80% confluency on 100 mm dishes and scraped in PBS at 4° C., centrifuged, and the cell pellets were frozen at −20° C. until analysis. Samples were thawed and whole homogenates were prepared as described and total glutathione (GSH+GSSG) was determined using a recycling method (Spitz, D. R.; Malcolm, R. R.; Roberts, R. J. Cytotoxicity and metabolism of 4-hydroxy-2-nonenal and 2-nonenal in H2O2-resistant cell lines. Do aldehydic by-products of lipid peroxidation contribute to oxidative stress? *Biochem J* 267:453-459; 1990; Griffith, O. W. Determination of glutathione and glutathione disulfide using glutathione reductase and 2-vinylpyridine. *Anal Biochem* 106: 207-212; 1980). All biochemical determinations were normalized to the protein content using the method of bicinchoninic acid protein assay.

Bicinchoninic Acid Protein Assay: Bicinchoninic acid protein assay was performed using the BCATM Protein Assay Kit from Pierce Biotechnology (Rockford, Ill.). The assay was performed according to manufacturer's instructions, using the "Enhanced Protocol."

Thioredoxin Reductase Assay: Thioredoxin Reductase activity was measured by using Thioredoxin Reductase Assay Kit purchased from Sigma (St Louis, Mo.). 400,000 cells/100 mm dishes of SUM159 cells were plated and treated with BSO, DTPP and AUR as described above. When cells were grown to 70-80% confluency on 100 mm dishes and scraped in PBS at 4° C., centrifuged, and the cell pellets were frozen at −20° C. until analysis. The assay was performed according to manufacturer's instructions. Briefly, working buffer containing 100 mM KPO4, pH 7.0, 10 mM EDTA, and 0.24 mM NADPH was prepared, and samples were added with working buffer along with 5,5'-dithiobis-(2-nitrobenzoic acid) (Eliman's reagent, DTNB). The rate of DTNB's reduction to 2-nitro-5-thiobenzoate (TNB) was then measured spectrophotometrically at 412 nM. For each sample, this reaction was replicated, in tandem, with the sample in the presence of an inhibitor to thioredoxin reductase (TrxR), included with the kit. The difference between the sample rate with and without the TrxR inhibitor was taken to be the difference caused by TrxR activity in the sample. Each sample was then normalized to protein, by using the Lowry protein assay, as described previously (Lowry, O. H.; Rosebrough, N.J.; Farr, A. L.; Randall, R. J. Protein measurement with the Folin phenol reagent. *J Biol Chem* 193:265-275; 1951). The thioredoxin reductase activity of each sample was then normalized as a percentage of that of the control cells.

Thioredoxin Redox Western: The human thioredoxin-1 protein level was determined by Thioredoxin redox western. Approximately 2-3 million treated or untreated SUM159 cells were lysed in G-lysis buffer (50 mM Tris-HCl, pH 8.3, 3 mM EDTA, 6 M guanidine-HCl, 0.5% Triton X-100) containing 50 mM iodoacetic acid (pH 8.3). The lysate was incubated in the dark for thirty minutes. The lysates were then centrifuged in G-25 microspin columns (GE Healthcare). Protein was then quantified, from the eluent by performing a Bradford protein assay, as previously described (Bradford, M. M. A rapid and sensitive method for the quantitation of microgram quantities of protein utilizing the principle of protein-dye binding. *Anal Biochem* 72:248-254; 1976). Equal amounts of protein were then added to a 15% acrylamide native gel. The gel was then run at 100 V for approximately 1.5 h. The proteins contained in the gel were then transferred to a nitrocellulose membrane (BIO-RAD Labs), using a semi-dry transfer protocol. The nitrocellose membrane was then washed in PBST (Phosphate buffered saline with 0.1% Tween) before being incubated at 4 overnight with the primary antibody, 1:1000 goat anti-hTrx-1 (American Diagnostica, Inc.) in PBST with 2% BSA. The primary antibody was then removed, the blot was washed in PBST for 10 minutes three times, with constant shaking, before being incubated for 1 h with the secondary antibody (Rabbit anti-goat IgG, HRP labeled (Santa Cruz Biotechnology). The blot was then washed again for 10 minutes three times in PBST before being treated with HRP chemiluminescence detection reagents (Renaissance, NEN). The protein was then visualized by exposing the blot to X-ray film for 2-5 min in a dark room with a film cassette, before developing the film.

Measure of AUR, DTPP and NAC interaction by Eliman's reagent To determine if NAC could direct react with AUR or DTPP, different concentrations of NAC, DTPP and AUR solutions were prepared. A NAC concentration standard curve were first constructed by adding different concentrations of NAC with DTNB and measuring spectrophotometrically the absorbance of DTNB's reduction to 2-nitro-5-thiobenzoate (TNB) at 412 nM. Then, equal moles of NAC, DTPP or AUR from each concentration were added together along with DTNB, respectively. For each combination, same moles of single agents were also added with DTNB. DMSO was added into NAC alone solution to maintain the same DMSO level in NAC+DTPP/AUR combinations. The absorbance of DTNB's reduction to 2-nitro-5-thiobenzoate (TNB) was then measured spectrophotometrically at 412 nM. For NAC and AUR interaction test, sample tubes were incubated in a 4%, 37° C. incubator for at least 1 h. For NAC and DTPP interation test, sample tubes were incubated in a 4%, 37° C. incubator for 24 h.

Spectrophotometric Electron Transport Chain Complex Activity Assays: Previous data demonstrate that TPP derivatives preferentially accumulate within cancer cell mitochondria, decrease the mitochondrial membrane potential, decrease oxygen consumption, and lead to an increase in free radical species. This data suggests that TPP derivatives act as inhibitors of the electron transport chain (ETC). To determine the specific mechanisms of action that TPP derivatives have on the ETC at the molecular level, we aimed to determine if decyltriphenylphosphonium (DTPP) inhibits one or more specific complex of the ETC. Spectrophotometric assays were performed on isolated mitochondria to evaluate how DTPP affects the activity of each ETC complex. Results show that DTPP significantly reduced the activity of complexes I and III, while negligible affects were observed in complexes II and W, thus supporting our preliminary data that TPP derivatives inhibit oxidative phosphorylation.

Liver mitochondria harvested for ETC assays: Livers were harvested from mice and placed in cold homogenizing medium (0.25 M sucrose, 5 mM hepes, 0.1 mM EDTA, 0.1% fatty acid free bovine serum albumin (BSA), (pH 7.25)). Samples were homogenized on ice using a glass dounce homogenizer and centrifuged at 1000×g for 10 mM at 4° C. Supernatants were transferred to high speed centrifuge tubes, while pellets were resuspended in cold homogenizing medium and reprocessed as described above. Supernatants were centrifuged at 10,000×g for 10 mM at 4° C. Supernatants were discarded and mitochondrial fractions were resuspended in cold potassium phosphate buffer (pH 7.25).

Assays: All assays were performed at 30° C. in 1.0 mL total volume using a Beckman Coulter DU 800 Spectrophotometer (Birch-Machin et al. 1994:35-42). The mitochondrial samples receiving treatment were incubated for 10 min in a high concentration of decyltriphenylphosphonium (DTPP), 500 uM to simulate the concentration of the compound in active, respirating mitochondria; however, final DTPP concentration in all complex activity assays was approximately 10 uM following sample dilution after the initial incubation. Total protein content was determined by Bradford assay (Biorad) and all electron transport chain enzyme activities were normalized to the total protein content.

The complex I activity assay measured the rate of absorbance change due to rotenone-inhibitable NADH oxidation ($\epsilon$=6.81 mM$^{-1}$ cm$^{-1}$). Mitochondria (resuspended in 20 mM potassium phosphate buffer, (pH 7.0)) were lysed due to freeze thawing and divided into four samples. Sample one contained complex I working buffer (25 mM potassium phosphate buffer (pH 7.2), 5 mM magnesium chloride, 2 mM potassium cyanide, 2.5 mg/mL BSA, 0.13 mM NADH), antimycin A (200 µg/mL), coenzyme Q1 (7.5 mM), and mitochondria (0.37 µg/µL). Sample two contained complex I working buffer, antimycinA, coenzyme Q1, rotenone (200 µg/mL), and mitochondria (0.37 µg/µL). Sample three contained complex I working buffer, antimycinA, coenzyme Q1, DTPP, and mitochondria (0.36 µg/µL). Sample 4 contained complex I working buffer, antimycin A, coenzyme Q1, rotenone, DTPP, and mitochondria (0.36 µg/µL). Samples were mixed and incubated for 1 mM at 30° C. Absorbance was read every 20 s for 3 min at 30° C. and the rate of absorbance change at 340 nm (reference wavelength=425 nm) was measured. Activity was calculated using the following formula: ($\Delta$Abs340-$\Delta$Abs340 Rot)/6.81/mg protein=µmmol/min/mg protein.

The Complex II activity assay measured the rate of absorbance change due to the reduction of 2,6-dichloroindophenol (DCIP) ($\epsilon$=19.1 mM$^{-1}$ cm$^{-1}$) by coenzyme Q in the presence and absence of succinate. Mitochondria (resuspended in 20 mM potassium phosphate buffer, (pH 7.0)) were lysed due to freeze thawing and divided into four samples. Sample one contained complex II working buffer (25 mM potassium phosphate buffer (pH 7.2), 5 mM magnesium chloride, 2 mM potassium cyanide, 2.5 mg/mL BSA), 25 mM potassium phosphate buffer, and mitochondria (0.37 µg/µL). Sample two contained complex II working buffer, 0.2 M succinate, and mitochondria (0.37 µg/µL). Sample three contained complex II working buffer, 25 mM potassium phosphate buffer, DTPP, and mitochondria (0.36 µg/µL). Sample four contained complex II working buffer, succinate, DTPP, and mitochondria (0.36 µg/µuL). Samples were mixed and incubated for 10 min at 30° C. Following incubation, antimycin A (200 µg/mL), rotenone (200 µg/mL), 5 mM DCIP, and 7.5 mM coenzyme Q1 were added to each cuvette and incubated for 1 min. The absorbance was read every 20 s for 3 min at 30° C. and the rate of absorbance change at 600 nm was measured. Activity was calculated using the following formula: ($\Delta$Abs600 Succinate-$\Delta$Abs600 No Succinate)/19.1/mg protein=µmol/min/mg protein.

The complex III activity assay measured the rate of absorbance change due to cytochrome c reduction (E=19.6 mM$^{-1}$ cm$^{-1}$) by coenzyme Q2. Coenzyme Q2 was reduced by adding 1 N HCl and potassium borohydride to 35 mM coenzyme Q2 until the reaction mixture turned from bright yellow to clear. The clear solution was transferred to a new tube and HCl was added to keep coenzyme Q2 reduced. Fresh mitochondria (resuspended in 20 mM potassium phosphate buffer, (pH 7.0)) were divided into four samples. Sample one contained complex III working buffer (25 mM potassium phosphate buffer (pH 7.2), 5 mM magnesium chloride, 2 mM potassium cyanide, 2.5 mg/ml BSA, 0.5 mM n-dodecyl $\beta$-maltoside), rotenone (200 µg/mL), 1.5 mM cytochrome c, and 3.5 mM coenzyme Q2. Sample two contained complex III working buffer, rotenone, cytochrome c, coenzyme Q2, and mitochondria (2.97 µg/µL). Sample three contained complex III working buffer, rotenone, cytochrome c, coenzyme Q2, and DTPP. Sample four contained complex III working buffer, rotenone, cytochrome c, coenzyme Q2, DTPP, and mitochondria (2.84 µg/µL). Samples were mixed and absorbance was read every 5 s for 1 min at 30° C. and the rate of absorbance change at 550 nm (reference wavelength=580 nm) was measured. Activity was calculated using the following formula: ($\Delta$Abs550mit-$\Delta$Abs550)/19.6/mg protein=µmol/min/mg protein.

The complex IV activity assay measured the rate of cytochrome c oxidation ($\epsilon$=19.6 mM$^{-1}$ cm$^{-1}$). Cytochrome c was reduced by adding 0.1 M dithiothreitol to cytochrome c. The reaction mixture was incubated on ice for 15 min until the reaction color changed from dark red to orange red. Mitochondria (resuspended in 20 mM potassium phosphate buffer, (pH 7.0)) were lysed due to freeze thawing and divided into two samples. Sample one contained complex IV working buffer (20 mM potassium phosphate buffer (pH 7.0), 0.5 mM n-dodecyl $\beta$-maltoside), 1.5 mM reduced cytochrome c, and mitochondria (0.37 µg/µL). Sample two contained complex IV working buffer, reduced cytochrome c, DTPP, and mitochondria (0.36 ug/uL). Absorbance was read every 20 s for 2 mM at 30° C. and the rate of absorbance change at 550 nm (reference wavelength=580 nm) was measured. Activity was calculated using the following formula: $\Delta$Abs550/19.6/mg protein=umol/min/mg protein.

Statistical Analysis: Statistical analysis was performed using GraphPad Prism version 4.00 for Windows (GraphPad Software, San Diego, Calif.). Data were expressed as mean±SEM unless otherwise specified. One-way ANOVA analysis with Tukey's post-analysis was used to study the differences among three or more means. Significance was determined at p<0.05 and the 95% confidence interval.

Figure 1B:
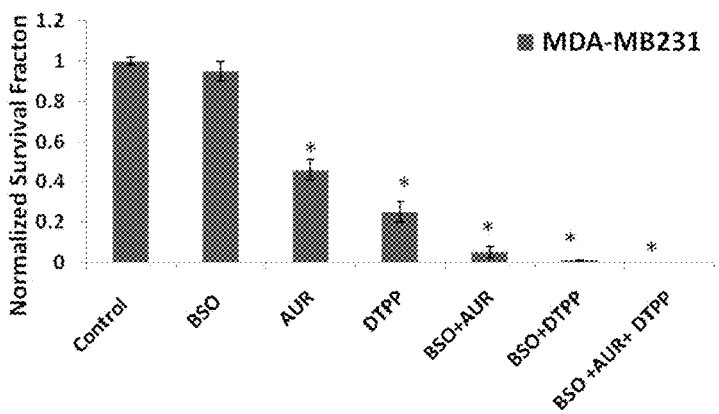
Figure 2:
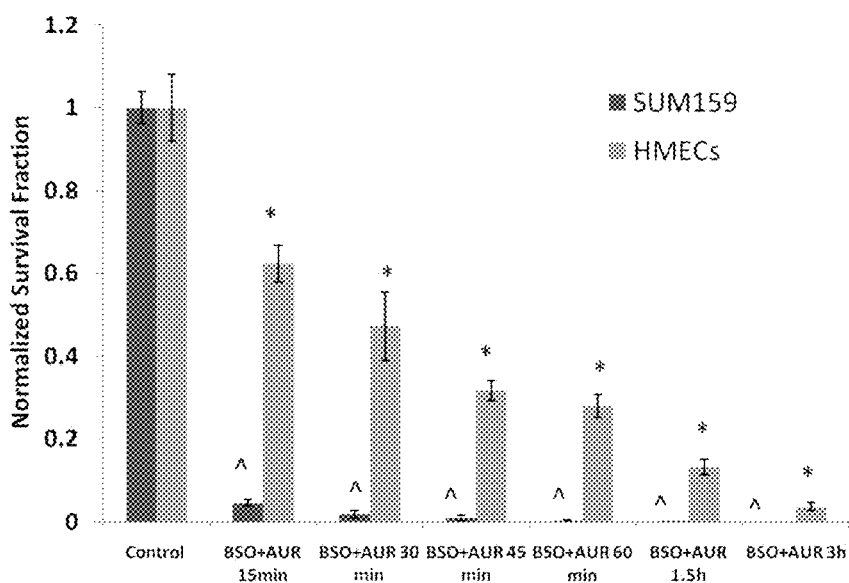
FIG. 2: BSO and AUR treated SUM159 dose response Clonogenic survival. 150,000 cells/dish SUM159 were plated in 60 mm tissue culture dishes. After 48 hours, cells were given fresh complete HMECs media and treated with 100 μM BSO 24 hours. 500 nM AUR were added 15 mins, 30 mins, 45 mins, 1 hr, 1.5 hrs and 3 hrs before the trypsinization. Cells were then collected and plated for clonogenic survival. In panel A-C, The error bars represent mean±1 SD of n=1 treatment dishes done in 3 separate experiments where each treatment dish was used to prepare 6-10 replicate cloning dishes for analysis. *p<0.001 as compared to SUM159 Control. ^p<0.001 as compared to HMEC Control. These results show that the drug combination of BSO and AUR is more toxic to cancer vs. normal human cells in a dose response fashion.

Results:

To determine if DTPP treatment could enhance the cytotoxicity mediated by the inhibitor of hydroperoxide (BSO), exponentially growing SUM159 and MDA-MB231 human breast cancer cells were treated with 100 µM BSO and/or 1 µM DTPP for 24 hours. Results in FIGS. 1A and B showed that treatment of exponentially growing SUM159 and MDA-MB231 cells with 1 µM DTPP for 24 hours caused a significantly decrease in cell survival (70%-80%) compared to control cells. Although BSO as a single agent alone did not cause significantly cytotoxicity to both cell lines, DTPP+BSO combination treatment caused the greatest decrease in survival fraction (95%-99%) compared to either agent alone. Since thioredoxin is also involved in hydroperoxide metabolism, 500 nM AUR was also added into certain groups to determine if using an inhibitor of thioredoxin reductase could further enhance the cytotoxicity in human breast cancer cells. Because our earlier studies suggested that 3 h AUR exposure with 24 h BSO pre-treatment was very toxic to both human breast cancer cells and HMECs, a time course of AUR cytotoxicity experiment was accomplished. Data in FIG. 2 clearly showed in 15 min AUR exposure, BSO+AUR could induce almost 95% clonogenic cell killing in SUM159 cells but only 40% clonogenic killing of HMECs. Although longer intervals of AUR exposure could further increase the cytotoxicity, the 15 min AUR exposure gave the widest therapeutic window between normal and cancer cells and therefore 15 min of AUR exposure was adopted for the following experiments. In FIGS. 1A and 1B, treatment of 500 nM AUR for 15 min further sensitized the BSO and DTPP induced cell killing in both cell lines. In SUM159 cells, 500 nM AUR treatment did not cause any significant cytotoxicity, however, BSO+AUR could induce nearly 90%-95% cell killing. When AUR was combined with BSO+DTPP, it could completely diminish the clonogenic cell survival in SUM159 cells. Interestingly, in MDA-MB231 cells 500 nM AUR itself could significantly induce nearly 50%-55% cell killing. Moreover, BSO+AUR or BSO+AUR+MitoQ drug combinations again significantly inhibit cell proliferation by decreasing the survival fraction to 5% and 0%, respectively.

Since the data showed that BSO+DTPP and/or AUR could induce such astonishing effects in human breast cancer cells, it is also important to know whether these drug combinations could affect HMECs. Exponentially growing HMECs were treated with BSO, DTPP and AUR as described above.

Figure 1C:
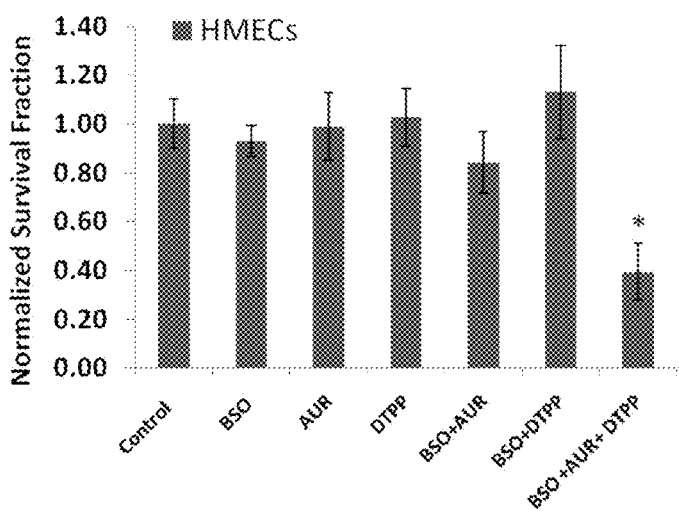

Data in FIG. 1C demonstrated that BSO, AUR, DTPP and BSO+DTPP did not cause any significant cytotoxicity in HMECs, suggesting that DTPP combined with BSO could induce selectively kill human breast cancer cells, relative to normal cells. Although BSO+AUR and BSO+AUR+DTPP induced around 25% or 60% clonogenic cell killing in HEMCs, respectively, the combinations still delivered much less cytotoxic effect compared to cancer cells. These data support the conclusion that DTPP combined with inhibitors of hydroperoxide (BSO, AUR) could induce significantly higher levels of clonogenic cell killing than a single agent alone in human breast cancer and also have less effect on human normal mammary cell reproductive integrity.

Figure 1D:
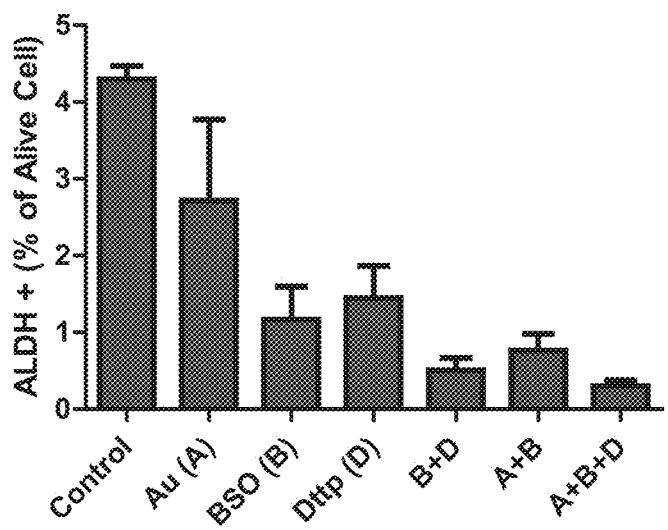

Because our earlier studies suggested that cancer stem cells also exhibited higher steady-state level of ROS compared to normal cells, we determined the effects of DTPP, BSO and AUR on cancer stem cell (CSC) populations. To address this question, SUM159 were treated with these drugs as described in FIG. 1, and aldehyde dehydrogenase (ALDH) activity, a marker of cancer stem cells was examined by ALDEFLUOR assay. ALDH is a detoxifying enzyme responsible for the reduction of intracellular aldehydes, which may have a role in early differentiation of stem cells through its role in oxidizing retinol to retinoic acid. Moreover, a recent study demonstrated that ALDEFLUOR-positive cells isolated from both normal and tumor human breast have phenotypic and functional characteristics of mammary stem cells. Results in FIG. 16 represent the percentage of ALDH positive cell of 100,000 cell events in each treatment group. From the table, it was noted that the average ALDH positive cells population in SUM 159 was around 2.61%. It is noted that BSO as a single agent alone was not able to decrease the ALDH positive cell population. In contrast, with AUR or DTPP treatment, the percentage of ALDH positive cell population decreased from 2.61% to 1.11% or 1.16%, respectively. Moreover, BSO+AUR, BSO+DTPP, BSO+DTPP+AUR combinations further decreased ALDH positive cells from 2.61% to 0.45%, 0.64%, and 0.17%, respectively. However, to ensure that these drug treatments could truly decrease the CSC population, an in vivo nude mouse experiment with SUM159 human breast cancer cells was performed. The results of this study showed that Aur+BSO+DTPP was also able to deplete ALDH positive cancer stem cells from human cancer cell populations in vivo grown as xenografts in nude mice (FIG. 1D).

Figures 3A, 3B:
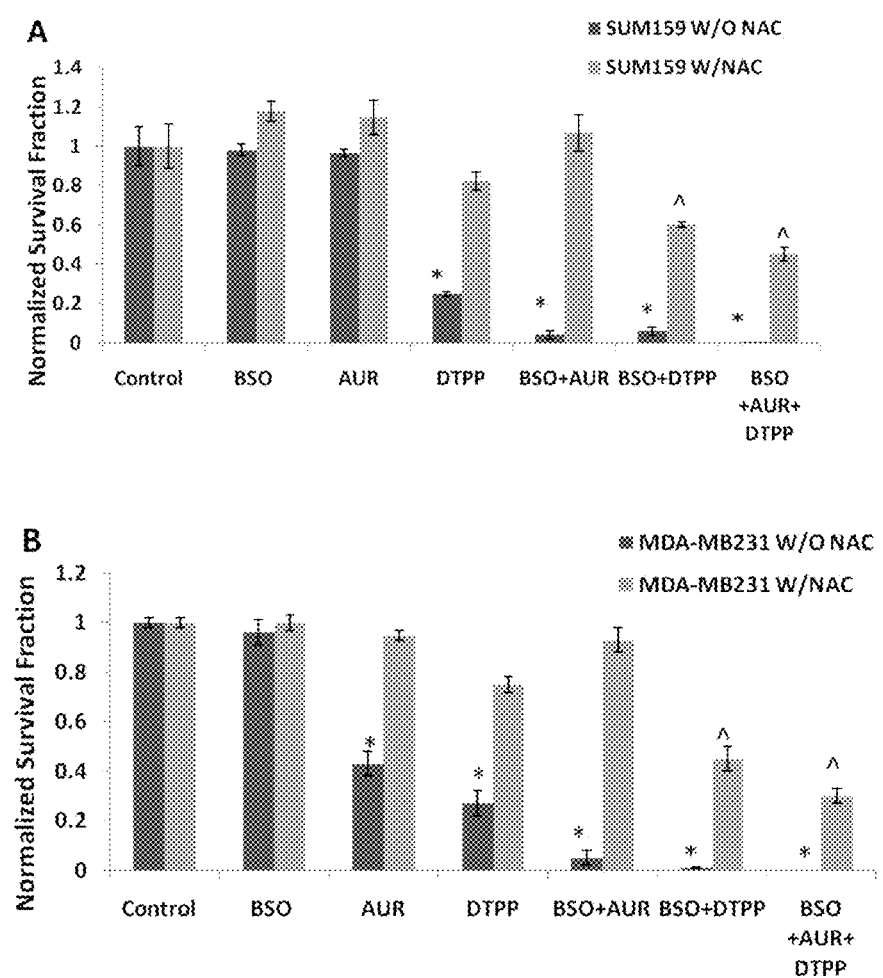
FIGS. 3A-3B: Clonogenic survival of SUM159 and MDA-MB231 cells treated with BSO, DTPP and AUR in the presence of 20 mM NAC. Asynchronously growing cultures of SUM159 (panel A) and MDA-MB231 (panel B) were plated as described in FIG. 1. After 48 hours, cells were given fresh complete HMECs media and treated with 100 μM BSO+/1 μM DTPP in the presence or absence of 20 mM NAC for 24 hours. 500 nM AUR were added 15 mins before the trypsinization. cells were then collected and plated for clonogenic survival. In panel A, B, The error bars represent mean±1SD of n=1 treatment dishes done in 3 separate experiments where each treatment dish was used to prepare 6-10 replicate cloning dishes for analysis. *p<0.001 as compared to W/O NAC Control. ^p<0.001 as compared to W/NAC Control. These results show that a thiol antioxidant (NAC) was capable of protecting human breast cancer cells from clonogenic cell killing mediated by AUR±BSO±DTPP supporting the claim that these drugs kill cancer cells by inducing oxidative stress.

To determine if oxidative stress was involved in DTPP combined with BSO and AUR induced cytotoxicity, SUM159 and MDA-MB231 cells were treated with 100 µM BSO, 1 µM DTPP and 500 nM AUR as previously described in the presence and absence of 20 mM NAC (a nonspecific thiol antioxidant) for 24 hrs. FIG. 3 shows that NAC was able to significantly inhibit DTPP induced clonogenic killing by increasing the survival fraction to at least 70% of control cells in both cell lines. More importantly, NAC was also demonstrated to be able to fully protect the SUM159 and MDA-MB231 cells from BSO+AUR induced toxicity and significantly rescue SUM159 and MDA-MB231 cells from clonogenic killing induced by BSO+DTPP and BSO+AUR+DTPP drug treatments. Furthermore, in order to confirm NAC could enter the cell in the reduced form to augment the intracellular thiol pool and protect the cells from BSO, AUR and DTPP toxicity but not directly react with them, an Ellman's regent test for interaction was accomplished. Ellman's reagent (5,5'-dithiobis-(2-nitrobenzoic acid) or DTNB) is a chemical used to quantify the number or concentration of thiol groups in a sample. Since NAC in the reduced form could cleave the disulfide bond to give 2-nitro-5-thiobenzoate ($NTB^-$), which further ionizes to a yellow color dianion ($NTB_2^-$), the NTB2$^-$ could be quantified in a spectrophotometer by measuring the absorbance of visible light at 412 nm. Therefore, NAC was combined with DTPP or AUR in equimolar concentrations to test if they could react with each other directly. FIG. 17 clearly shows that the 412 nm absorbance of the NAC+DTPP group with 24 hr incubation was same as that of NAC alone, suggesting there is no direct chemical interaction between NAC and DTPP during the drug treatment. Interestingly, the 412 nm absorbance of NAC+AUR is the sum of the absorbance of NAC and AUR alone, which indicates that AUR was able to reduce DTNB. This might be due to the gold cation, which can facilitate cleavage of the S—S bond of the disulfide in DTNB and further reduce to $NTB_2^-$. This could have some significance for how AUR is able to inhibit thioredoxin reductase activity but the mechanistic details of the reaction should be further explored. Because absorbance of the combination group equals the sum of two single drugs, the data in FIG. 17 also shows that there is no direct reaction between NAC and AUR that is capable of inactivating AUR. Given all these facts, these results support the conclusion that metabolic oxidative stress plays a causal role in BSO+DTPP+AUR-mediated breast cancer cell killing in a thiol dependent fashion that this toxicity is inhibited by a thiol antioxidant.

Figures 4A, 4B, 4C:
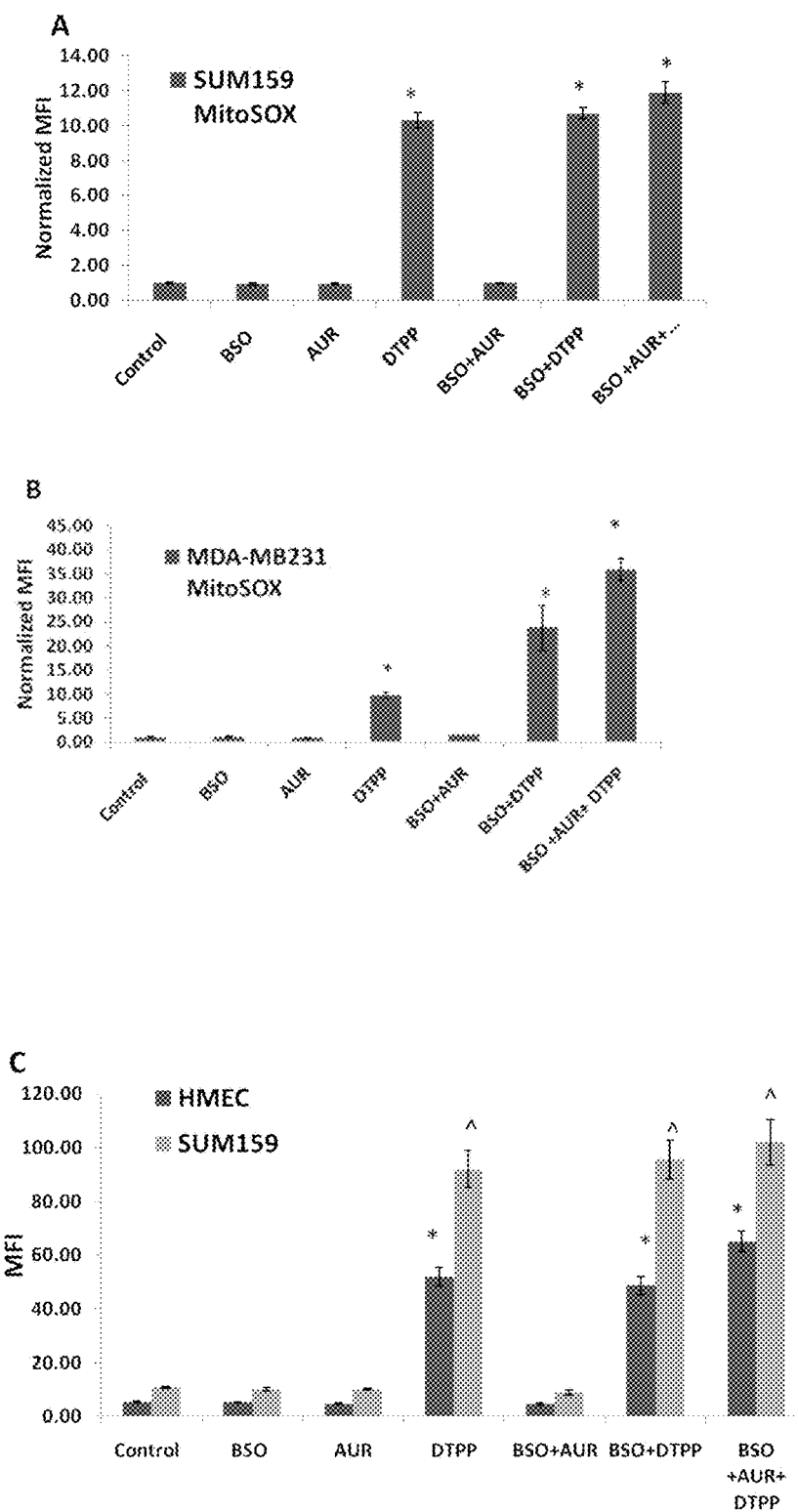
FIGS. 4A-4C: MitoSOX oxidation in SUM159, MDA-MB231 and HMECs cells treated with BSO, DTPP and AUR. Asynchronously growing cultures of SUM159 (Panel A) MDA-MB231 (Panel B) and HMECs (Panel C) were plated and treated as described in FIG. 1. Monolayer cultures were harvested and trypsinized, washed once with PBS and labeled 20 minutes with 2 μM MitoSOX (in 0.1% DMSO) in PBS containing 5 mM pyruvate at 37° C. Each sample was then analyzed for the Mean fluorescence Intensity (MFI) of 10,000 cells by flow cytometry. Samples were assayed in triplicate; mean±1 SD of 1 experiment containing 3 treatment dishes per group (n=3), * or ^p<0.001 as compared to Control. These results show that DTPP increases mitochondrial levels of superoxide and that this happens to a greater extent in cancer vs. normal human cells.

As aforementioned, DTPP could significantly enhance the clonogenic cell killing mediated by BSO and AUR and this toxicity can be protected by NAC. This result suggested that DTPP might exhibit its biological effects by increasing oxidative stress and thiol oxidation in SUM159 and MDA-MB231 cells. Because intracellular levels of reactive oxygen species (ROS) such as superoxide and hydrogen peroxide play an important role in oxidative stress, and mostly importantly, DTPP is a mitochondrial targeted cationic lipophilic molecule, it is possible that DTPP could interfere with the mitochondrial electron transport chain leading to more one electron reductions of O2 to form superoxide and hydrogen peroxide which could further react with oxygen to generate superoxide. To determine if DTPP exposure could increase mitochondrial ROS and further contribute to oxidative stress and deleterious biological effects, the steady state level of superoxide was determined by measuring MitoSOX red (a mitochondrial superoxide specific fluorescence probe) oxidation. When SUM159 and MDA-MB231 cells were exposed to 1 µM DTPP for 24 h, significant 9- and 12-fold increases (relative to control) in MitoSOX red oxidation were observed in both cell lines (FIG. 4A,4B). Similar 10-fold increases of MitoSOX oxidation were also noticed in BSO+DTPP and BSO+DTPP+AUR treated SUM159 cells (FIG. 4A). In MDA-MB231 cells (FIG. 4B), even greater increases were noted in MitoSox oxidation in BSO+DTPP and BSO+DTPP+AUR treatment groups (20-fold, 30-fold compared to control, respectively). Interestingly, BSO, AUR and BSO+AUR treatment groups did not exhibit any change in MitoSOX oxidation, though BSO+AUR induce significant clonogenic cell killing. These results may suggest that intracellular steady-state levels of mitochondrial $O_2.^-$ were significantly increased after DTPP exposure and this increased steady-state level of mitochondrial $O_2.^-$ could contribute to the toxic effects caused by DTPP.

Because there is a great increase in MitoSOX oxidation (indicative of increase of steady-state level of mitochondrial $O_2.^-$) after DTPP treatment, it is also important to know if DTPP could also affect the steady-state level of mitochondrial $O_2.^-$ in HMECs. Thus, HMECs and SUM159s received similar drug treatment as afore-mentioned in FIG. 4C and the steady-state levels of mitochondrial $O_2.^-$ were compared. In FIG. 4C, showed 10-fold increases in MitoSOX oxidation in the DTPP, BSO+DTPP and BSO+AUR+DTPP treated groups. However, based on the basal differences between the normal cell and cancer cells, it is still clear that the total amount of increase in MitoSOX oxidation in cancer cells is still 2-fold higher than normal cells. BSO, AUR and BSO+AUR were also found to have no effects on MitoSOX oxidation. However, confocal microscopy with MitoSOX and Mitotracker dual labeling in the absence or presence of AdMnSOD transduction should be done to fully confirm that the signal truly represents mitochondrial $O_2.^-$.

Figures 5A, 5B, 5C, 5D:
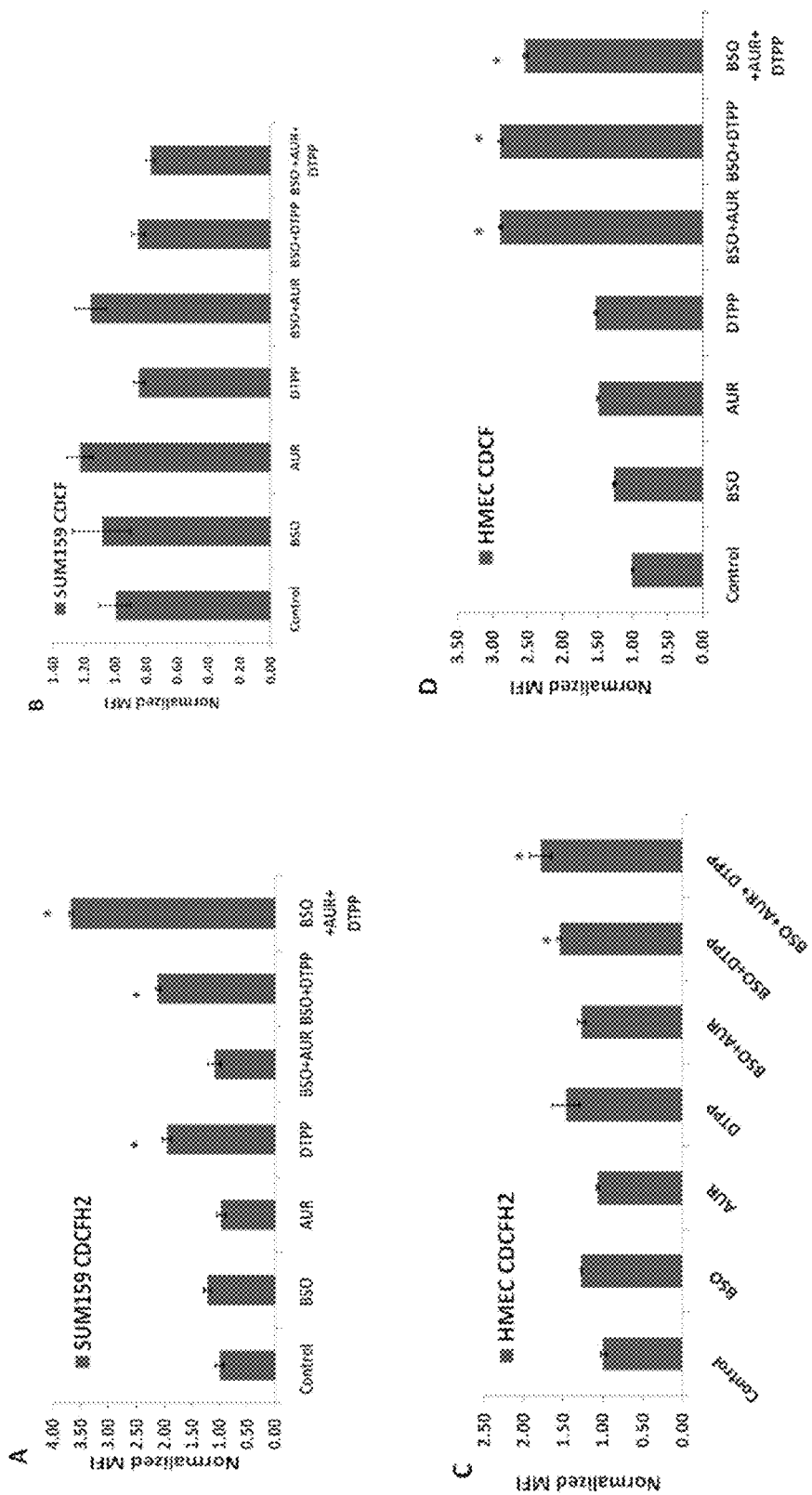
FIGS. 5A-5D: CDCFH$_2$ oxidation sensitive and CDCF oxidation insensitive probe labeling of BSO, DTPP, and AUR exposed SUM159 and HMECs cells. Asynchronously growing cultures of SUM159 (Panels A, B) and HMECs (Panes C, D) were plated and treated as described in FIG. 1. Monolayer cultures were harvested and trypsinized, washed once with PBS then labeled in PBS with either CDCFH$_2$ (Panesl A, C) or CDCF (Panels B, D)(10 μg/mL, in 0.1% DMSO 15 minutes) at 37° C. Mean fluorescence intensity (MFI) of 10,000 cells was analyzed by flow cytometry. Samples were assayed in triplicate; Mean±1 SEM of 3 separate experiments containing 3 treatment dishes per group (n=9), *p<0.001 as compared to Control. These results support the claim that these drug combinations selectively increase hydroperoxide levels in cancer vs. normal cells.

To determine if the intracellular steady-state levels of hydroperoxides were also increased in SUM159 human breast cancer cells and human normal mammary epithelial cells treated with BSO, AUR and DTPP, cells were labeled with the oxidation-sensitive probe $CDCFH_2$ after 24 h treatment with 100 μM BSO and 1 μM DTPP in the presence or absence of 500 nM AUR. $CDCFH_2$ crosses cellular membranes and is enzymatically hydrolysed by "intracellular" esterases, and then can be further oxidized to produce a green fluorescent compound (CDCF) trapped inside of the cell for detection by flow cytometry. In SUM159 cells, there was a significant 2-fold increase in $CDCFH_2$ oxidation (FIG. 5A) in cells treated with DTPP or BSO+DTPP, and when SUM159 cells were treated with BSO+AUR+DTPP, the $CDCFH_2$ oxidation was even further increased (3-4 fold increase compared to control). To further confirm that changes in $CDCFH_2$ oxidation truly represented changes in probe oxidation, the previous experiment was also repeated using the oxidation-insensitive analog (CDCF), which measures changes in dye uptake, ester cleavage, and efflux (independent of oxidation). The results showed that DTPP, BSO+DTPP and BSO+AUR+DTPP slightly decreased CDCF fluorescence compared to control cells, suggesting that any increases in oxidation noted with $CDCFH_2$ were clearly indicative in changes in probe oxidation (FIGS. 5A and 5B). When the experiment was repeated using HMECs, data in FIG. 5C and FIG. 5D showed that DTPP, BSO+DTPP and BSO+AUR+DTPP induced 1.5-2 fold increases in $CDCFH_2$ oxidation, relative to control cells. However, unlike DTPP treated SUM159 cells, the CDCF labeling signal in HMECs treated with DTPP, BSO+DTPP and BSO+DTPP+AUR was actually 2-fold higher than control (FIG. 5D). This result suggested that the increase in fluorescence of $CDCFH_2$ labeled normal cells after DTPP exposure was not due to changes in probe oxidation but likely due to the changes in dye uptake, ester cleavage, and efflux. Overall, these results suggested that DTPP combined with BSO and AUR could selectively increase the $CDCFH_2$ (indicative of steady-state level of hydroperoxides) oxidation in cancer cells relative to normal HMECs. It is therefore possible that this difference in CDFH2 oxidation could have significantly contributed to the DTPP induced oxidative stress and other deleterious effects that were selectively seen in cancer vs. normal cells.

Figure 6:
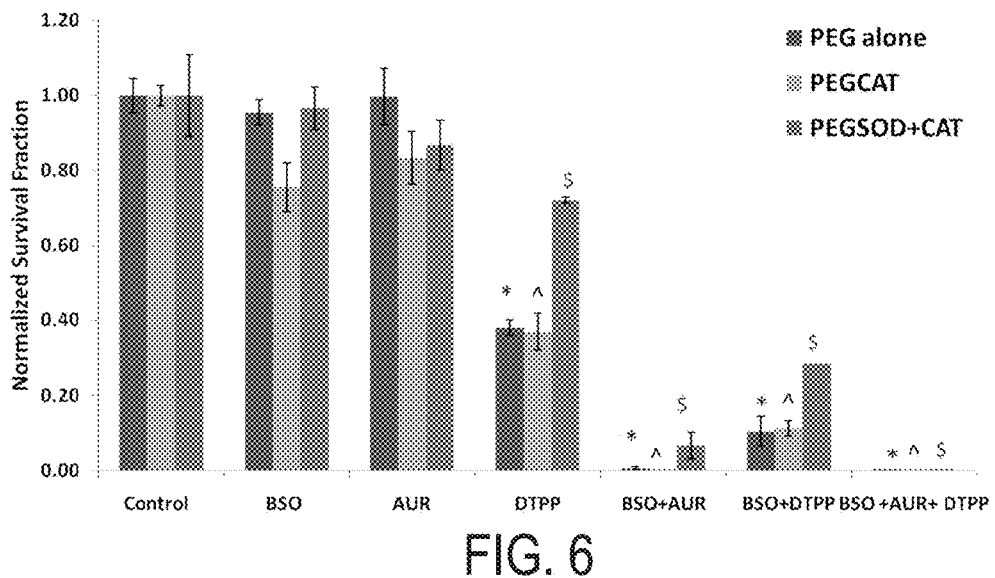
FIG. 6: BSO, DTPP and AUR treated SUM159 in the presence of 100 U/ml PEGSOD+/PEGCAT Clonogenic survival. Asynchronously growing cultures of SUM159 were plated as described in FIG. 1. After 48 hours, cells were given fresh complete HMECs media and treated with 100 μM BSO+/1 μM DTPP in the presence or absence of PEGSOD+/PEGCAT (100 U/mL each) for 24 hours. Control received PEG alone (18 μM) for 24 hours. 500 nM AUR were added 15 mins before the trypsinization. Cells were then collected and plated for clonogenic survival. In panel A, B, The error bars represent mean±1 SD of n=1 treatment dishes done in 3 separate experiments where each treatment dish was used to prepare 6-10 replicate cloning dishes for analysis. *p<0.001 as compared to PEG alone Control. ^p<0.001 as compared to PEGCAT Control, $ p<0.001 as compared to PEGSOD+CAT Control. These results show that the toxicity of these drug combinations is mediated at least in part by superoxide and hydrogen peroxide.

To determine the role of specific ROS (i.e., $O_2.^-$ and $H_2O_2$) in cell killing induced by BSO, DTPP and AUR, SUM159 cells was treated with BSO, DTPP and AUR as in FIG. 1 in the presence and absence of 100 U/ml PEGSOD (a specific $O_2.^-$) and/or PEGCAT (a specific $H_2O_2$ scavenger). PEGCAT was not found to be able to inhibit DTPP, BSO+AUR, BSO+DTPP and BSO+DTPP+AUR induced toxicity in SUM159 cells (FIG. 6). However, PEGSOD+PEGCAT together appeared to protect cells from DTPP and BSO+DTPP induced clonogenic cell killing in SUM159 (from 35% to 70% and 10% to 30%, respectively) (FIG. 6). Since results in FIGS. 4 and 5 showed DTPP could significantly increase the MitoSOX and $CDCFH_2$ oxidation, it is interesting to find that PEGCAT and PEGSOD could only modestly protect SUM159 cancer cells from DTPP induced toxicity. However, this data still provides evidence that, 1) the increased $CDCFH_2$ signal might not be the result of $H_2O_2$ mediated oxidation of the CDFH2 probe but could be do to some other prooxidant (as yet to be identified) and this fact may explain why PEGCAT could not protect SUM159 cells from DTPP induced toxic effects; 2) Since the MitoSOX data suggested that the primary site of increased $O_2.^-$ was in mitochondria, it is possible that due to the size of the PEG molecule, PEG-SOD was not able to pass into the mitochondrial membrane to maximize its superoxide scavenging ability at the site of superoxide production. Overall, this data provides clear evidence to support the hypothesis that $O_2.^-$ is at least in part responsible for the enhanced cytotoxicity seen when early exponential growth phase human breast cancer cells are treated with DTPP+BSO/BSO+AUR.

Based on the above results, DTPP was shown to significantly increase the $CDCFH_2$ oxidation (indicative of increased prooxidant production) in SUM159 cells. Since GSH or Trx are important small molecule thiol antioxidants necessary for detoxifying hydroperoxides and other species capable of oxidizing critical thiol residues in proteins, we wanted to know if DTPP induced could increase steady-state level of ROS that could be synergistically enhanced with BSO and AUR to maximize their toxicity towards cancer cells. Therefore, levels of total GSH and GSSG were measured in drug treated SUM159 cells to determine if disruptions in glutathione metabolism were involved in the oxidative stress and toxicity caused by BSO, AUR, DTPP. In FIG. 18, when SUM159 cells were treated with BSO for 24 hours, significant decreases in total GSH were noted vs. control. Although DTPP only modestly decreased the total GSH level, when BSO was combined with DTPP or DTPP+AUR, total GSH was reduced below the detection limit. Moreover, SUM159 treated with DTPP also showed around a 3-fold increase in GSSG (from 0.06 to 0.26 nmole GSSG/mg protein) and % GSSG (from 1.13% to 3.65%), compared to untreated cells. It was also noted that BSO and BSO+AUR could significantly increase the % GSSG from 1.13% to 4.88% and 10.81%, respectively. These data showed that AUR as a single agent was not capable of altering the glutathione metabolism compared to control. Based on these findings, it is noted that DTPP could modestly affect glutathione metabolism. However, DTPP is a mitochondrial targeted molecule, and DTPP did induce increased steady-state levels of ROS from mitochondria. Therefore, a mitochondrial GSH analysis should also be accomplished to fully understand if DTPP could selectively affect mitochondrial GSH metabolism.

Figure 7:
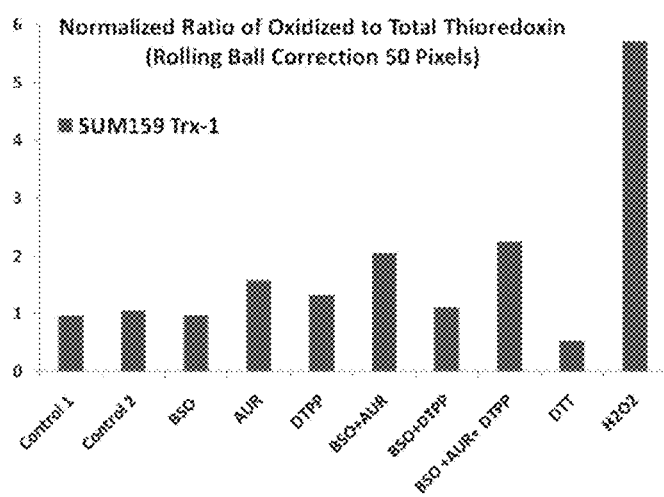
FIG. 7: Human thioredoxin-1 (hTrx-1) native redox western blot analysis of BSO, DTPP and AUR treated SUM159. Asynchronously growing cultures of SUM159 were plated and treated as described in FIG. 1. Cells were harvested and scraped in PBS at 4° C. Whole cell homogenates were used for native gel redox western blot analysis of thioredoxin reductase activity. The results show that these drug combinations induce oxidative stress in the cancer cells.

To determine if DTPP induced increased oxidative stress in the thioredoxin system, a native gel redox western blot of human Trx 1 was accomplished. In FIG. 7, when SUM159 cells were treated with AUR, BSO+AUR or BSO+DTPP+AUR, the ratio of oxidized thioredoxin to total thioredoxin was increased around 2-fold compared to control. This result suggests that AUR could increase the oxidized thioredoxin by inhibiting the thioredoxin reductase (TRR) activity. When SUM159 cells were treated DTPP or BSO+DTPP for 24 hours, the ratio of oxidized thioredoxin to total thioredoxin only showed a modest increase. There is no ratio change in BSO treated SUM159 cells. Based on these result that it is hard to elucidate the relationship between thioredoxin and increased ROS production after DTPP exposure. However, since DTPP is thought to be mitochondrially targeted and might exhibit its effect in mitochondria, a redox western blot determination of the mitochondrial localized thioredoxin 2 oxidation state could be beneficial to obtain further insights into the mechanism of DTPP-induced oxidative stress and its effects on thioredoxin metabolism.

Figure 8:
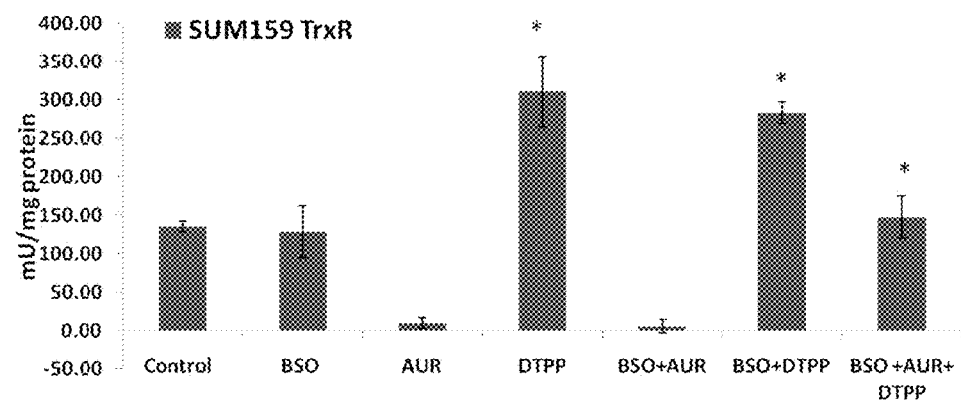
FIG. 8: Intracellular thioredoxin reductase (TRR) activity measured in BSO, DTPP, and AUR exposed SUM159 cells. Asynchronously growing cultures of SUM159 were plated and treated as described in FIG. 1. Cells were harvested and scraped in PBS at 4° C. Whole cell homogenates were used for biochemical analysis of thioredoxin reductase activity. Errors represent Mean±1 SD of 4 samples from two separate experiments (n=4). *p<0.001 as compared to Control. These results show that AUR inhibits TRR activity and DTTP induced TRR activity.
Figure 9:
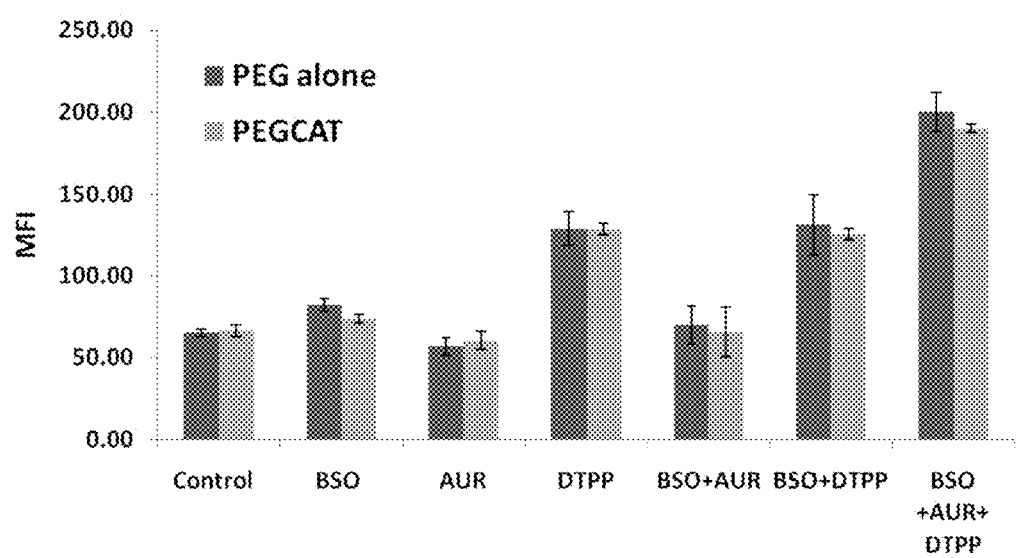
FIG. 9: Catalase inhibitable CDCFH$_2$ oxidation in BSO, DTPP, and AUR exposed SUM159 cells. Asynchronously growing cultures of SUM159 were plated and treated as described in FIG. 1. 100 U/ml PEG-CAT or 18 μM PEG alone were given 2 hours before and during CDCFH$_2$ labeling to cells. Monolayer cultures were harvested and trypsinized, washed once with PBS then labeled in PBS with either CDCFH$_2$ (10 μg/mL, in 0.1% DMSO 15 minutes) at 37° C. Mean fluorescence intensity (MFI) of 10,000 cells was analyzed by flow cytometry. Samples were assayed in triplicate; Mean±1 SD of 1 separate experiments containing 3 treatment dishes per group (n=3). These results show that PEG-CAT was incapable of inhibiting CDCFH2 oxidation under these conditions.

Another key component of thioredoxin metabolism is thioredoxin reductase, which was suggested to be able to exhibit pro-survival signaling and help cancer cells to escape oxidative stress induced cytotoxicity. Our results suggested that using an inhibitor of TRR (AUR) could significantly sensitize cancer cells to BSO cytotoxicity. It is also of interest to explore if DTPP treatment could also alter the thioredoxin metabolism by changing TRR activity. When SUM159 cells treated with BSO, AUR, DTPP as previously described, data in FIG. 8 showed that 15 min AUR exposure could significantly inhibit TRR activity, decreasing from 135 mU/mg protein to 10 mU/mg protein. A similar result is also noted in BSO+AUR treated SUM159, in which the activity decreased from 135 mU/mg protein to 7 mU/mg protein. These data confirm that AUR acts as an inhibitor of TRR and could exhibit its effects in a short period time. It is also shown that BSO alone was not capable of altering the TRR activity, compared to control. Most surprisingly, DTPP or BSO+DTPP treatment could induce significant 2-fold increases of TRR activity (from 135 mU/mg to 311 mU/mg or 283 mU/mg, respectively). Even with the 15 min AUR treatment, DTPP could partially reverse the BSO+AUR induced inhibition of TRR activity. It is very interesting to observe that DTPP could increase the TrxR activity while still causing significant cytotoxic effects. It is possible that this TRR activity increase might act as an adaptive response against the cytotoxicity caused by DTPP induced-oxidative stress. Alternatively the TRR activity increase could be due to an adaptive response to elevated oxidized Thioredoxin by DTPP exposure. Since we did not see a significantly increase in oxidized hTrx-1, again, this data again suggests that more experiments (i.e., hTrx-2 western blot) should be accomplished to fully understand the mechanisms and consequences of DTPP induced TRR activity.

Figure 11:
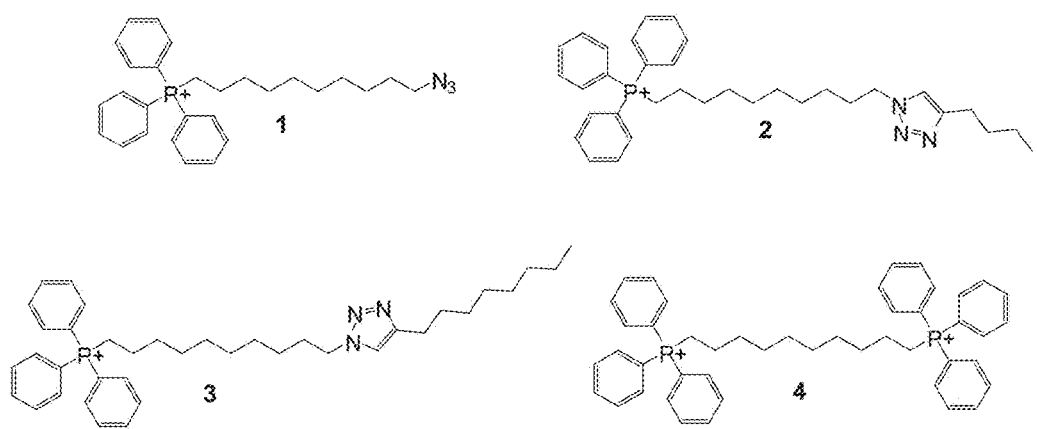
FIG. 11: TPP variants synthesized to examine the effect molecular chain substituents on cancer cell specific cytotoxicity.

To determine the significance of the molecular chain substituent changes to the TPP in relation to cancer cell specific cytotoxicity, clonogenic assays were performed with MB231 and Hec50co cells using TPP variants synthesized in our laboratory (FIG. 11). Variants synthesized included (10-azidodecyl)triphenylphosphonium (1), which was used as a linchpin for synthesis of variants (10-(4-butyl-1H-1,2,3-triazol-1-yl)decyl)triphenylphosphonium (2) and (10-(4-octyl-1H-1,2,3-triazol-1H-yl)decyl)triphenylphosphonium (3), as well as decane-1,10-diylbis(triphenylphosphonium) (4). DecylTPP and pentylTPP were also examined and were obtained commercially.

Figure 12:
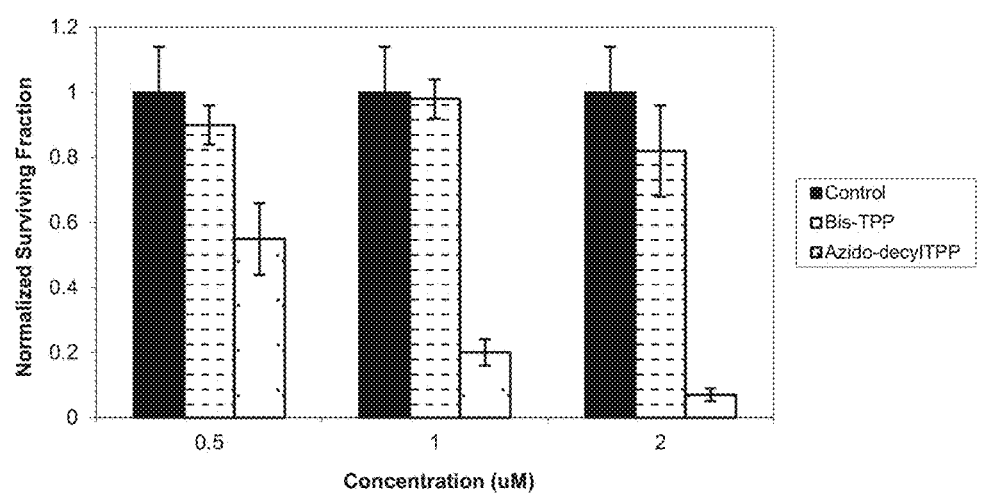
FIG. 12: Azido-decylTPP and Bis-TPP MB231 clonogenic assay. These data show that increasing concentrations of azido-decylTPP have a dose dependent cytotoxic effect on breast cancer cells, while the bis-decylTPP compound does not in human cancer cells. MB231 cells were treated with 0.5 μM, 1.0 μM, and 2.0 μM azido-decylTPP and bis-TPP and incubated for 24 hrs. DMSO was added to control dishes to a final concentration of 0.1%. Following a 24 hr. incubation period, cells were plated at densities of 200, 400, 600, 800, and 2,000 cells per dish and incubated for 2 weeks. After incubation, cells were stained with Coomassie blue and counted under a light microscope. Survival fraction was calculated by dividing the number of colonies counted following treatment by the product of the number of cells plated and plating efficiency. Error bars represent uncertainties. N=2. These results show that the decyl chain of the DTPP molecule must be free to insert into the mitochondrial membrane to induce cytotoxicity in the human cancer cells.
Figure 13:
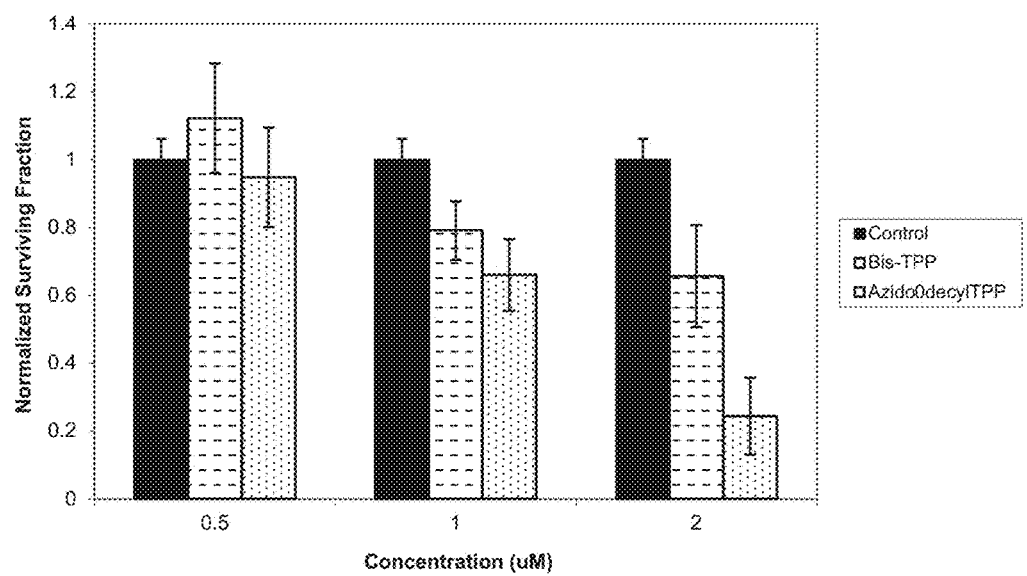
FIG. 13: Azido-decylTPP and Bis-TPP Hec50co clonogenic assay. These data show that increasing concentrations of azido-decylTPP have a dose dependent cytotoxic effect on human endometrial cancer cells, while the bis-decylTPP compound has a more modest effect in Hec50co cells. Hec50co human endometrial cancer cells were treated with 0.5 μM, 1.0 and 2.0 μM azido-decylTPP and bis-TPP and incubated for 24 hrs. DMSO was added to control dishes to a final concentration of 0.1%. Following a 24 hr. incubation period, cells were plated at densities of 200, 400, 600, 800, 2,000, 5,000, and 10,000 cells per dish and incubated for 2 weeks. After incubation, cells were stained with Coomassie blue and counted under a light microscope. Survival fraction was calculated by dividing the number of colonies counted following treatment by the product of the number of cells plated and plating efficiency. Error bars represent uncertainties of N=2 experiments.
Figure 14A:
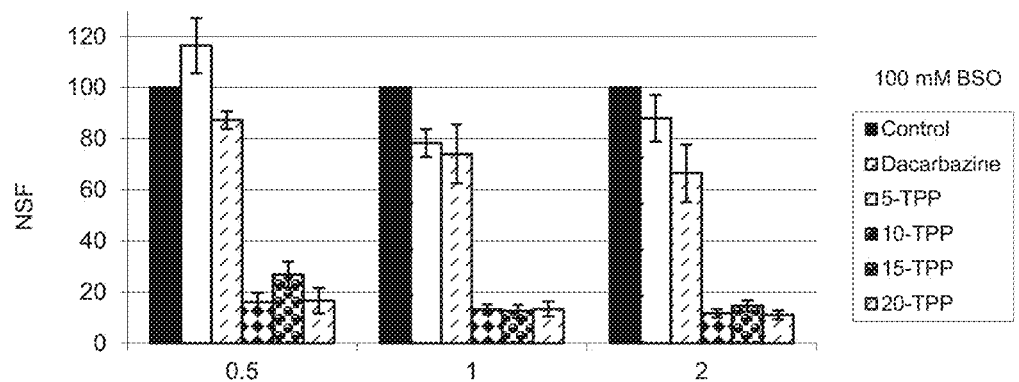
FIGS. 14A-14B: MTT survival fraction analysis of A375 melanoma cells looking at the effect of variation in TPP molecular chain substituent length in the presence and absence of BSO with comparison to standard of care dacarbazine: (A) pentyl-TPP has little cytotoxicity in the presence of BSO up to 2 μM concentration, while TPP conjugates with longer tails 10, 15, 20 atoms have significant cytotoxicity in the presence of BSO; (B) The cytotoxicity of a TPP conjugate with a 20 carbon chain length in the tail function has significant cytotoxicity in the absence of BSO, while the effect is lessened for shorter tail conjugates. These data further demonstrate the effect of the molecular substituent on cytotoxicity.
Figure 14B:
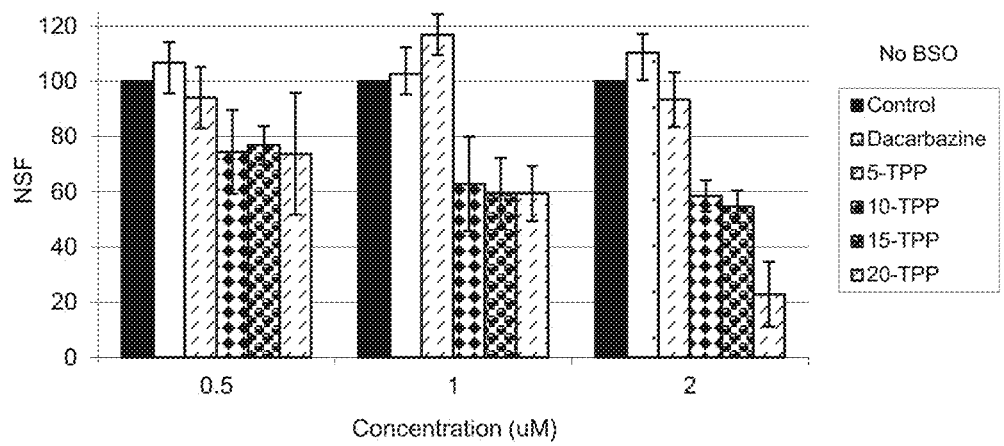

In FIG. 11, when MB231 cells were treated with 0.5 uM azido-DTPP, a survival fraction of 55% was observed compared to 90% in cells treated with 0.5 uM bis-DTPP. At concentrations of 2 uM, 10% of azido-DTPP cells survived compared to 82% in bis-DTPP treated cells. In FIG. 12, similar results were demonstrated in Hec50co cells. At a concentration of 2 uM, a 24% survival fraction was observed in azido-DTPP treated cells compared to 66% in bis-DTPP treated cells. Further, reduced cytotoxicity was observed when A375 melanoma cells were treated with pentyl-TPP in the presence of BSO (70% survival fraction at 2 µM pentylTPP, compared to <20% survival fraction for TPP bioconjugates with tail lengths 10, 15, and 20 atoms (FIG. 13A). In addition, a TPP conjugate functionalized with a 20 atom tail exhibited significant cancer cell cytotoxicity in the absence of BSO, while the pentyl-TPP variant had no effect on these cells under the same conditions and the penta-DTPP and DTPP variants showed intermediate cytotoxicity (FIG. 13B). These results suggest that the molecular chain substituent is a key reactive component in cancer cell cytotoxicity rather than the TPP moiety of the bioreactive conjugates.

Figure 15:
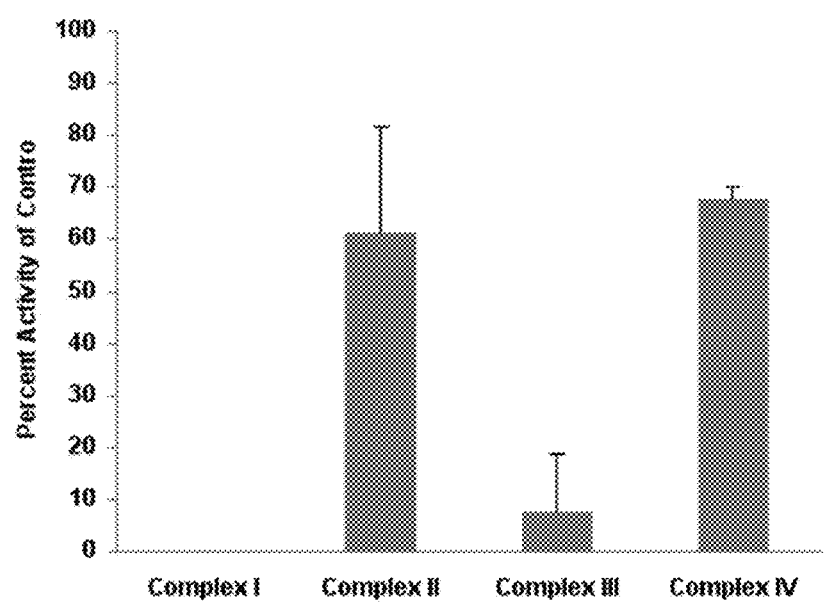
FIG. 15: DTPP treated mitochondria electron transport chain activity assays looking at the specific mitochondrial electron transport chain complexes that TPP based compounds inhibits. The activity of electron transport chain complexes I-IV was measured spectrophotometrically in mitochondria treated with 10 uM DTPP. Error bars represent uncertainties of n=2 experiments. These results indicate that DTPP selectively inhibits electron transport chain complex I and III activity relative to untreated controls.

To determine the specific electron transport chain protein complexes that are inhibited by TPP based compounds, spectrophotometric assays were performed on isolated mitochondria to evaluate how DTPP affects the activity of each ETC complex. Results show that DTPP significantly reduced the activity of complexes I and III, while negligible affects are attributed to inhibition of complexes II and IV, thus supporting our preliminary data that TPP derivatives inhibit oxidative phosphorylation and lead to increased oxidative stress (FIG. 15).

Overall, these data from the above experiments show that DTPP and other XTPP variants of differing tail composition and characteristics are pro-oxidants in cancer cells and can significantly enhance oxidative stress by increasing the steady-state levels of mitochondrial ROS, and this increased oxidative stress could be further enhanced by inhibitors of hydroperoxide metabolism in human breast cancer cells, and melanoma cells relative to normal human mammary cells.

Discussion:

Recent studies have suggested that cancer cells are under persistent oxidative stress because of increased steady-state levels of superoxide and hydroperoxides, relative to normal cells. Moreover, it has been also clearly documented that cancer cells have altered antioxidant levels (i.e., SOD, CAT, GSH). In order to cope with these excessive ROS, cancer cells have been hypothesized to increase glycolysis and pentose phosphate cycle activity to compensate for excess hydroperoxide production by direct deacetylation of hydroperoxides by pyruvate (formed during glycolysis), as well as regeneration of NADPH in the pentose cycle, which could provide electrons for glutathione and thioredoxin dependent peroxidase systems. Therefore, the inventors hypothesized that the increased dependency of cancer cells on the glucose and hydroperoxide metabolism to protect cancer cells from hydroperoxides-induced lethal effects could be utilized to develop novel therapeutic interventions for the treatment of cancer. By taking advantage of this hypothesis, two main strategies were proposed: firstly, inhibition of the antioxidant system of detoxifying hydroperoxide in cancer cells; secondly, increasing the metabolic production of ROS causing oxidative stress (i.e., hydroperoxide and/or superoxide) in cancer cells.

Glutathione is one of the most important small molecule antioxidants in the detoxification of hydroperoxides; decreased glutathione levels would induce incapability of hydroperoxides removal. Moreover, GSH also played an important role in tumor drug resistance. Therefore, inhibitors of hydroperoxides metabolism, by depleting GSH levels, have been tested in cancer therapy. BSO is a relatively specific inhibitor of gamma-glutamylcysteine synthetase, the rate-limiting step in GSH synthesis. However, BSO as a single agent in cancer therapy was not very effective in some clinical trials possibly because of redundancy of in peroxide metabolic pathways. It is also known that anti-cancer treatment developments that focus on agents that target a single molecule or signaling pathway are unlikely to meet the expectation due to the versatile nature of tumor cells. Thus, adding other toxic agents with BSO treatment should be considered.

The excessive ROS production in cancer cells compared to normal cells might provide conditions for selectively targeting the cancer cells with agents that can increase the ROS production and result in oxidative stress mediated cell death in cancer cells, while normal cells should possess enough antioxidants to deal with the extra ROS production. Therefore, an agent that can increase the metabolic ROS production combined with an inhibitor of hydroperoxide production should be anticipated to further preferentially kill cancer cells, relative to normal cells. Additionally, recent research showed that mitochondrial electron transport chain blockers (ETCB) like Antimycin A (Ant A) or rotenone (Rot) could increase steady-state levels of $O_2.^-$, and $H_2O_2$; cause the accumulation of glutathione disulfide; and enhance 2DG-induced cell killing. Furthermore, studies also pointed out that mitochondria may be the major source of pro-oxidant production during the 2DG exposure. It is therefore logical to predict that inhibiting glucose and hydroperoxide metabolism while increasing the mitochondrial ROS production could contribute to the excess oxidative stress in cancer cells, and this increase of oxidative stress could preferentially kill cancer cells relative to normal cells.

To test this hypothesis, DTPP was applied in this study. DTPP is a lipophilic cation, which can pass directly through phospholipid bilayers due to its large hydrophobic surface area lowering the activation energy for uptake, and which accumulates further into mitochondria. It has been suggested that mitochondrial accumulation of lipophilic cations could increase the permeability of the mitochondrial inner membrane and inhibit mitochondrial enzymes nonspecifically, affecting mitochondrial ROS production, inhibiting respiration, and leading to cell death. Studies also have been suggested that lipophilic cations could be used as anti-cancer drugs because many cancer cells have a higher mitochondrial membrane potential than normal cells, which could lead to selective uptake. It has also been shown that lipophilic cations can disrupt cell function and selectively kill the cancer cells in vivo and in vitro. However, there is relatively little knowledge about the mechanism of how DTPP induces mitochondrial dysfunction and ROS production. Since the TPP$^+$ group is thought to associate with the phospholipid head groups at the mitochondrial inner membrane matrix surface, while the decyl chain could insert to the bilayer, it is possible that the inserted chain could affect the electron transport chain in mitochondria and increase the probability of one electron reductions of $O_2$ to form superoxide. It is also possible that the selective accumulation of DTPP in cancer cell mitochondria might inhibit mitochondrial respiration, a major pathway to provide reducing equivalents. Moreover, damage to the mitochondria can cause changes in mitochondrial permeability and the release of apoptotic factors that could further contribute to the DTPP induced cell death in human breast cancers, relative to normal cells. Therefore, we hypothesized that DTPP might affect mitochondrial function by increasing mitochondrial ROS and further contribute to the toxicity of inhibitors of hydroperoxide metabolism.

In this study, when exponentially growing SUM 159 and MDA-MB231 human breast cancer cells were treated with 100 µM BSO and/or 1 µM DTPP for 24 hours, it was observed that treatment of BSO as a single agent was tolerated in both cancer cell lines. In contrast, DTPP could induce at least 70% clonogenic cells killing in both cell lines. When DTPP was combined with BSO treatment, clonogenic survival of both cell lines was even further decreased, suggesting that BSO significantly enhanced DTTP induced cytotoxicity (FIGS. 1A, 1B). Furthermore, when the same exposure was applied to the HMECs, DTPP, BSO or BSO+DTPP did not show any effects on HMEC's reproductive integrity, suggesting differential susceptibility between human cancer cells and human normal cells (FIG. 1C). These data strongly support the hypothesis that BSO could increase the DTTP-induced cytotoxicity in human cancer cells.

Besides GSH and Glutathione reductase, another thiol redox system found in cells is thioredoxin reductase (TRR) and thioredoxin (Trx). In this model, TRR is a selenocysteine-containing protein that catalyzes the reduction of Trx using NADPH as a reducing agent. Under oxidative stress, Trx could undergo thiol±disulfide exchange catalyzed by Trx peroxidase to detoxify $H_2O_2$. It has also been shown that TrxR initiates a pro-survival signaling cascade in response to ROS induced cytotoxicity. Moreover, recent research demonstrated that the TRR/Trx system could also contribute to many other cell functions including DNA synthesis, gene transcription, cell growth and transformation, and resistance to cytotoxic agents that induce oxidative stress and apoptosis. These observations suggest that TRR might represent an attractive candidate for a potential target in response to oxidizing agents.

To explore if inhibiting Trx metabolism could further increase DTPP and/or BSO induced cytotoxicity, a relatively specific inhibitor of TRR, AUR, a gold(I)-based drug class utilized in the treatment of rheumatoid arthritis was used. Results in FIGS. 1A and 1B showed that AUR as an single agent did not cause too much toxicity in SUM159, but induced 50% clonogenic cell killing in MDA-MB231, suggesting that further analysis on the Thioredoxin metabolism of the two cell lines is needed to address this question. When AUR was combined with BSO, the combination induced similar cytotoxicity on cell proliferation as BSO+DTPP. When the three agents were combined together, they could induce 100% clonogenic cell killing in MDA-MB231 and SUM159. These data suggested that simultaneous inhibition of the two hydroxide detoxification pathways could even further enhance the cancer cell killing.

BSO and/or DTPP treatment on HMECs did not cause any cytotoxic effect. Therefore, AUR could significantly sensitize MDA-MB231 and SUM 159 to the BSO or BSO+DTPP combination but without affecting the proliferation of HMECs. Although some clonogenic cell killing was noted in the in HMECs, BSO+AUR and BSO+AUR+DTPP treatments still induced selective cell killing in SUM159 and MDA-MB231 cells compared to HMECs (FIG. 1C). Overall, these results are all consistent with the hypothesis that addition of a thioredoxin reductase inhibitor (AUR) could even contribute to DTPP+/BSO-induced clonogenic cell killing in human breast cancer cells.

Recent research in a large variety of tumors showed the existence of cancer stem cell (CSC). It was suggested that tumors contain and are driven by these stem cells, which have the properties of self-renewal, and the capacity to generate cellular heterogeneity. Studies also demonstrated that CSC could play an important role in tumor progression and malignancy and the development of specific therapeutics that target this population could significantly enhance cancer therapy. Since DTPP combined with BSO and/or AUR induced remarkable cytotoxicity, it is also important to determine if these drug treatments could decrease the CSC population in human breast cancer cells. Therefore, SUM159 were treated as in FIG. 1 and ALDH activity was determined by ALDEFLUOR assay. Results in FIG. 16 showed BSO alone did not decrease the population of ALDH positive cells whereas AUR alone or DTPP alone could decrease this population to around 50%. Moreover, when BSO was combined with DTPP or AUR+DTPP, these combinations even more significantly decreased the ALDH positive cell population. Although further determination of whether these signals were truly representative of the CSC population is needed, this result suggested BSO, DTPP and AUR exposure could deplete the CSC population. And these results also indicate targeting the intrinsic ROS difference between cancer stem cells and normal cells might be an effective approach in cancer therapy.

To establish that oxidative stress was causally related to the enhanced cell killing seen in the presence of DTPP, cells were treated with BSO, DTPP and AUR in the presence of a nonspecific thiol antioxidant, NAC. The results in FIG. 3 showed that NAC successfully suppressed cell killing in breast cancer cells treated with DTPP, BSO+AUR, BSO+DTPP and BSO+DTPP+AUR. Furthermore, it is clear that NAC suppressed the DTPP or AUR toxicity by augmenting the thiol pool inside the cells instead of reacting with DTPP or AUR outside cells, as shown by the Ellman's reagent assay described in FIG. 17. This finding demonstrated that the clonogenic cell killing caused by DTPP was due to oxidative stress.

To understand the origin of DTPP induced oxidative stress, a series of ROS measurement experiments were done. MitoSOX oxidation was prominently increased in any treatment group including DTPP in both SUM159 and MDA-MB231 (FIGS. 4A and 4B). Although the results also suggested that DTPP could induced similar fold increases in HMECs, it is important to note that HMEC's basal MitoSOX oxidation (indicative of steady-state level of $O_2.^-$) is 2-fold lower compared to SUM159's basal level (FIG. 4C). This basal level difference indicates that DTPP induced a similar fold increase of mitochondrial $O_2.^-$ production in HMECs, but the total amount of mitochondrial $O_2.^-$ of SUM159 cells is still 2-fold higher than that of HMECs. Once it is generated in the cell, $O_2.^-$ could either spontaneously, or through the action of superoxide dismutase enzymes, undergo dismutation to form $H_2O_2$ which also could adversely affect cell growth and proliferation. Additionally, excessive superoxide could also react with lipids and proteins to form other organic hydroperoxides and or aldehydes. Therefore, to determine if DTPP could also increase hydroperoxide production, a $CDCFH_2$ oxidation assay (indicative of hydroperoxides) was performed. The results in FIGS. 5A and 5B showed that in SUM159 cells, DTPP alone or DTPP+BSO could significantly increase the $CDCFH_2$ oxidation and BSO+DTPP+AUR could even further increase the $CDCFH_2$ oxidation. When similar experiments were accomplished in HMECs, though, an increase in $CDCFH_2$ fluorescence was also observed (FIG. 5C). However, a CDCF oxidation-insensitive probe experiment suggested that this might due to the changes in dye uptake, ester cleavage, and efflux instead of probe oxidation (FIG. 5D). These results together with previous experiments together suggested that 1) DTPP could selectively induce the higher steady-state level of mitochondrial $O_2.^-$ and hydroperoxides in human breast cancer cells compared to HMECs and this difference might contribute to the differential cytotoxicity caused by DTPP exposure; 2) even though there is an increase in steady-state level of mitochondrial superoxide in HMECs with DTPP treatment, the antioxidant system in normal cells might be adequate to deal with this to prevent further cytotoxcity.

Figure 10:
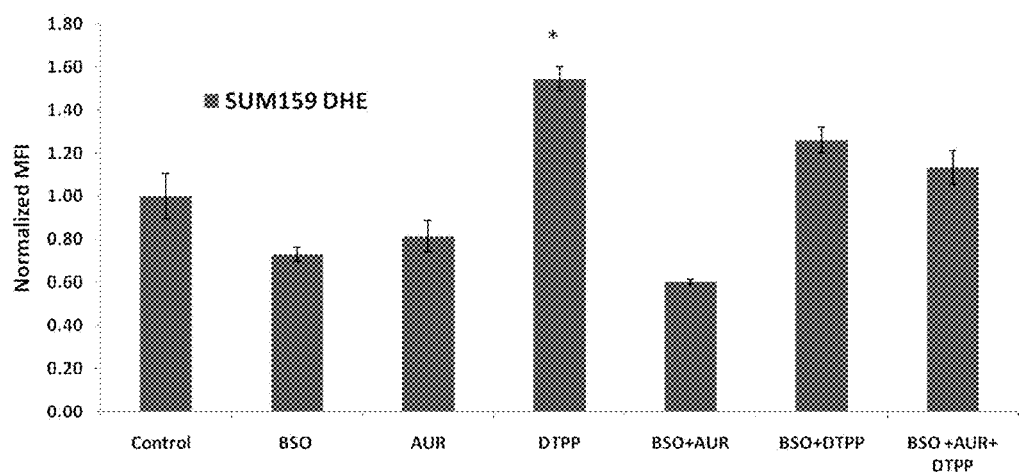
FIG. 10: DHE oxidation of BSO,DTPP and AUR exposed SUM159 cells. Asynchronously growing cultures of SUM159 were plated and treated as described in FIG. 1. Monolayer cultures were harvested and trypsinized, washed once with PBS and labeled 40 minutes with 5 μM DHE (in 0.1% DMSO) in PBS containing 5 mM pyruvate at 37° C. Each sample was then analyzed for the Mean fluorescence Intensity (MFI) of 10,000 cells by flow cytometry. Samples were assayed in triplicate; mean±1 SD of 2 experiment containing treatment dishes per group (n=6). *p<0.001 as compared to Control. These results indicate that only modest increases in DHE oxidation occurred in cancer cells treated with DTPP, which when compared to FIG. 4 results with MitoSox shows that mitochondrial superoxide is relatively more important that cytosolic superoxide for the drug-induced effects.

To determine if oxidative stress mediated by increased steady-state levels of mitochondrial $O_2.^-$ and $H_2O_2$ contributed to DTPP induced clonogenic cell killing, a PEGSOD+/PEGCAT rescue were accomplished. Results in FIG. 6 showed PEGCAT as a single agent was not capable of protecting SUM159 cells from DTPP induced cytotoxcity. Results also showed that PEGSOD+CAT only modestly increased the clonogenic survival in the DTPP and BSO+DTPP treated SUM159. Since DTPP has been shown to be able to increase the MitoSOX oxidation and $CDCFH_2$ oxidation, and it is also noted that DTPP could cause significantly clonogenic cell killing, it is interesting to determine why PEGCAT and PEGSOD did not significantly suppress DTPP induced toxicity in SUM159 cancer cells. There are some possible reasons: 1) These data suggest the increases of the $CDCFH_2$ oxidation might not come from $H_2O_2$. Since $CDCFH_2$ can be oxidized by many hyperoxides, nitric oxide derivatives, enzymes, and redox active metal ions it is possible that other pro-oxidants may be involved in cell killing mediated by these drug combinations. This might be able to explain why PEGCAT could not protect SUM159 cells from DTPP induced toxicity. 2) DHE oxidation results (FIG. 10) showed there was only 1.5 fold increase of DHE oxidation in DTPP treated SUM159 cells and there is even less increase in DHE oxidation in BSO+DTPP and BSO+AUR+DTPP treated groups. This result implied that the increased $O_2.^-$ might mainly happen in the mitochondria and not in the cytosol. Moreover, since the enzymes (SOD or CAT) are conjugates with PEG, which is a relatively large molecule for mitochondrial membrane transport, they might not able to enter the mitochondria to exhibit their effects. Because of this, it is possible that PEGSOD+PEGCAT could only modestly rescue the SUM159 from cytotoxicity caused by BSO, AUR, DTPP. 3) It is also possible that if there is more free iron or copper ions available, the increased steady-state level of $O_2.^-$ and $H_2O_2$ could start Fenton reactions to generate hydroxyl radicals. Since the hydroxyl radical is highly reactive and hard to scavenge, this could also contribute to the less protective effect seen in this experiment. To test the hypothesis that the mitochondria are the primary site of ROS production and mitochondrial targeted antioxidant enzyme could better protect cells from DTPP caused cytotoxicity, over expression of AdMnSOD and/or AdMitoCAT should be tested. To test if metal ions are also participating in the DTPP induced toxicity, metal chelators should be administered together with DTPP to see if cancer cells can be rescued from this cytotoxicity.

Because the increased steady-state level of hydroperoxides might also affect thiol metabolism, Glutathione levels, a thioredoxin redox Western blot and TrxR activity were investigated after BSO, DTPP, AUR exposure. Results in FIGS. 7, 8 and FIG. 18 showed BSO and AUR worked as they are reported. In a glutathione assay, BSO as a inhibitor of GSH synthesis successfully decreased the total GSH level and increased % GSSG (FIG. 18) and AUR did not change the total GSH, GSSG and % GSSG. However, for DTPP, it was noticed that DTPP did not change the total glutathione level but could modestly increase the GSSG and % GSSG in SUM159 cells (FIG. 18). In Trx-1 and TrxR assay, 15 min AUR was able to significantly decrease TrxR activity and induce a 2-fold increase of the ratio of oxidized Trx-1 to reduced Trx-1 (FIGS. 7 and 8). In contrast, DTPP was not able to change the ratio of oxidized to reduced Trx-1, but could induce a 2-fold increase of TrxR activity (FIGS. 7 and 8). It is unclear why changes were caused by DTPP exposure. For the glutathione assay, we only measured the whole cell GSH level and it is possible as afore-mentioned that the primary site of ROS production is mitochondria. Thus it is possible a mitochondrial GSH assay will be better way to investigate the role of DTPP on glutathione metabolism. Since there are different types and locations of thioredoxin in the cell, it is difficult to conclude the mechanism by which DTPP alters thioredoxin metabolism based on Trx-1 analysis alone. However, there could be two possible reasons that DTPP induced elevated TRR activity. The TrxR activity increase could be caused by cancer cell up-regulation of TRR activity to act against the DTPP caused cytotoxicity. Additionally, it is possible that elevated mitochondrial ROS production after DTPP exposure could lead to an increased ratio of oxidized to reduced Trx-2. This increase of Trx-2 oxidation might further activate TRR to more efficiently recycle the oxidized Trx-2.

To further establish the mechanism of action of TPP based drugs, spectrophotometric assays were carried out on isolated mitochondria to determine the specific ETC protein complex interactions with TPP based drugs that drive superoxide production. These assays demonstrated that TPP based drugs interact with and inhibit complexes I and III, while little interaction was observed with complexes II and IV in the mitochondrial ETC.

In conclusion, this study provides support for the hypothesis that TPP based drugs, a potential stimulator of mitochondrial pro-oxidant production, could increase the clonogenic cell killing in the presence of inhibitors of hydroperoxides metabolism by selectively increasing the steady-state levels of mitochondrial superoxide and hydroperoxides in human breast cancer cells and melanoma cells, relative to human mammary epithelial cells. These results further demonstrate that the mechanism of action is related to interaction of the TPP based compounds with electron transport chain protein complexes I and III, while little interaction is observed with complexes II and IV of the ETC. These results are encouraging because the efficacy of cancer therapy largely depends on the ability of cytotoxic agents to selective kill cancer versus normal cells based on fundamental differences in metabolism between cancer vs. normal cells. Since BSO, AUR, and TPP based drugs are all well tolerated in normal tissue, our findings provide a biochemical rationale for the development of new drug combinations to enhance susceptibility to cancer therapies.

Abbreviations:
2DG 2-deoxy-d-glucose
AUR (S-triethylphosphinegold(I)-2,3,4,6-tetra-O-acetyl-1-thio-b-Dglucopyranoside
Auranofin
ALDH aldehyde dehydrogenase
BSO L-buthionine-[S,R]-sulfoximine
CDCFH$_2$ 5-(and-6)-carboxy-2',7'-dichlorodihydrofluorescein diacetate
CSC Cancer Stem Cell
TPP triphenylphosphonium
DHE dihydroethidium
DMSO dimethyl Sulfoxide
ETCs electron transport chains
GSH glutathione
H$_2$O$_2$ hydrogen peroxide
MFI mean fluorescence intensity
MOI multiplicity of infection
NAC N-acetyl-cysteine
O$_2$.$^-$ superoxide
PBS phosphate buffered saline
PEG-CAT polyethylene glycol conjugated catalase
PEG-SOD polyethylene glycol conjugated CuZn superoxide dismutase
ROS reactive oxygen species
SOD superoxide dismutase
Trx Thioredoxin
TRR Thioredoxin reductase All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for treating lung cancer in a mammal, comprising administering to the mammal a pharmaceutical composition comprising a decyl-TPP agent that increases reactive oxygen species (ROS) levels in cancer cell mitochondria, an inhibitor of hydroperoxide metabolism, and a pharmaceutically acceptable diluent or carrier.

2. The method of claim 1, wherein the composition does not significantly inhibit viability of comparable non-cancerous cells.

3. The method of claim 1, wherein the cancer is reduced in volume by at least 10% as compared to a non-treated cancer.

4. The method of claim 3, wherein tumor uptake of a molecular imaging agent is reduced by any amount between 1-100% as compared to a non-treated cancer.

5. The method of claim 4, wherein the imaging agent is fluorine-18 deoxyglucose, fluorine-18 thymidine or other suitable molecular imaging agent.

6. The method of claim 1, wherein the composition is administered intraveneously, orally, subcutaneously, as an aerosol, or by means of another approved mode of pharmaceutical administration.

7. The method of claim 6, wherein the composition is administered at a dosage of 5-200 micromol/kg/day of decyl-TPP agent agent.

8. The method of claim 1, wherein the inhibitor of hydroperoxide comprises L-buthionine-[S,R]sulfoximine (BSO).

9. The method of claim 1, further comprising feeding the mammal a ketogenic diet.

10. The method of claim 1, further comprising administering pharmacological doses of IV vitamin C.

11. A method for inducing cellular apoptosis or clonogenic cell killing of a cancerous lung cell, comprising contacting the cancerous lung cell with an effective toxicity-inducing amount a composition comprising a decyl-TPP agent that increases reactive oxygen species (ROS) levels in cancer cell mitochondria, an inhibitor of hydroperoxide metabolism, and a pharmaceutically acceptable diluent or carrier.

12. The method of claim 11, wherein the inhibitor of hydroperoxide comprises L-buthionine-[S,R]sulfoximine (BSO).

13. A method for increasing the anticancer effects of a lung cancer therapy on a cancerous lung cell in a mammal, comprising contacting the cancerous cell with an effective amount of the composition comprising a decyl-TPP agent that increases reactive oxygen species (ROS) levels in cancer cell mitochondria, an inhibitor of hydroperoxide metabolism, and a pharmaceutically acceptable diluent or carrier, and contacting prior to administering an additional cancer therapy.

14. The method of claim 13, wherein the inhibitor of hydroperoxide comprises L-buthionine-[S,R]sulfoximine (BSO).

15. A method for inducing oxidative stress in a lung cancer cell in a mammal in need of such treatment comprising administering to the mammal an effective amount of the composition comprising a decyl-TPP agent that increases reactive oxygen species (ROS) levels in cancer cell mitochondria, an inhibitor of hydroperoxide metabolism, and a pharmaceutically acceptable diluent or carrier.

16. The method of claim 15, wherein the inhibitor of hydroperoxide comprises L-buthionine-[S,R]sulfoximine (BSO).

* * * * *

UNITED STATES PATENT AND TRADEMARK OFFICE
CERTIFICATE OF CORRECTION

PATENT NO. : 9,801,922 B2  
APPLICATION NO. : 14/236879  
DATED : October 31, 2017  
INVENTOR(S) : Douglas R. Spitz et al.

Page 1 of 1

It is certified that error appears in the above-identified patent and that said Letters Patent is hereby corrected as shown below:

In the Claims

Column 39, Line 7, Claim 7, please delete "decyl-TPP agent agent." and insert -- decyl-TPP agent. -- therefor.

Signed and Sealed this
Sixth Day of November, 2018

Andrei Iancu
*Director of the United States Patent and Trademark Office*